(12) United States Patent
Dredge

(10) Patent No.: US 11,298,369 B2
(45) Date of Patent: Apr. 12, 2022

(54) COMPOSITION AND USES THEREOF

(71) Applicant: Progen PG500 Series Pty Ltd, Victoria (AU)

(72) Inventor: Keith Dredge, Geelong (AU)

(73) Assignee: Progen PG500 Series Pty Ltd, Geelong (AU)

( * ) Notice: Subject to any disclaimer, the term of this patent is extended or adjusted under 35 U.S.C. 154(b) by 0 days.

(21) Appl. No.: 16/442,061

(22) Filed: Jun. 14, 2019

(65) Prior Publication Data

US 2019/0314393 A1 Oct. 17, 2019

Related U.S. Application Data

(63) Continuation-in-part of application No. PCT/AU2017/051402, filed on Dec. 15, 2017.

(30) Foreign Application Priority Data

Dec. 15, 2016 (AU) .................................. 2016905199

(51) Int. Cl.
| | | |
|---|---|---|
| A01N 43/04 | (2006.01) |
| A61K 31/70 | (2006.01) |
| A61K 31/704 | (2006.01) |
| A61P 35/00 | (2006.01) |
| A61K 39/395 | (2006.01) |
| A61K 39/00 | (2006.01) |

(52) U.S. Cl.
CPC ...... *A61K 31/704* (2013.01); *A61K 39/39558* (2013.01); *A61P 35/00* (2018.01); *A61K 2039/505* (2013.01)

(58) Field of Classification Search
None
See application file for complete search history.

(56) References Cited

U.S. PATENT DOCUMENTS

| 7,875,592 B2 | 1/2011 | Ferro et al. |
| 8,828,952 B2 | 9/2014 | Ferro et al. |
| RE46,955 E | 7/2018 | Ferro et al. |

FOREIGN PATENT DOCUMENTS

| WO | WO 2015/069770 | 5/2015 |
| WO | WO 2015/176033 | 11/2015 |
| WO | WO 2016/061142 | 4/2016 |

OTHER PUBLICATIONS

Winterhoff et al. European Journal of Cancer (2015), vol. 51, pp. 879-892.*
Mashima et al. OncoTargets and Therapy (2015), vol. 8, pp. 2045-2051.*
Blumenschein, "An Open-label Randomized Phase III Trial of BMS-936558 versus Docetaxel in Previously Treated Advanced or Metastatic Squamous Cell Non-small Cell Lung Cancer," (URL https://clinicaltrials.gov/archive/NCT01642004/2016_04_14), published Apr. 14, 2016 according to clinicaltrials.gov archive, retrieved from the internet Sep. 13, 2019.
"Cancer immunotherapy," Wikipedia (URL:https://en.wikipedia.org/w/index.php?title_Cancer_immunotherapy&oldid=754246015#Immune_checkpoints) retrieved from the internet on Jul. 3, 2019.
Dredge et al., "PG545, a dual heparinase and angiogenesis inhibitor, induces potent anti-tumour and anti-metastatic efficacy in preclinical models," *British Journal of Cancer* 104(4):635-642, 2011.
Jung et al., "The heparan sulfate mimetic PG545 interferes with Wnt/β-catenin signaling and significantly suppresses pancreatic tumorigenesis alone and in combination with gemcitabine," *Oncotarget* 6(7):4992-5004, 2014.
Millward, "Study of the Safety and Tolerability of PG545 in Patients with Advanced Solid Tumours," (URL: https://clinicaltrials.gov/archive/NCT01252095/2012_08_01), published Aug. 1, 2012 according to clinicaltrials.gov archive, retrieved from the internet Sep. 13, 2019.
Millward, "Study of the Safety and Tolerability of IV Infused PG545 in Patients with Advanced Solid Tumours," (URL: https://clinicaltrials.gov/archive/NCT02042781/2016_11_30), published Nov. 30, 2016 according to clinicaltrials.gov archive, retrieved from the internet Sep. 13, 2019.
Boyango et al., "Heparanase Cooperates with Ras to Drive Breast and Skin Tumorigenesis," *Cancer Research* 74(16):OF1-OF11, Aug. 15, 2014.

(Continued)

*Primary Examiner* — Patrick T Lewis
(74) *Attorney, Agent, or Firm* — Klarquist Sparkman, LLP

(57) ABSTRACT

The present invention relates, inter alia, to methods for the prevention or treatment of cancer, and to compositions, combinations and kits for the treatment or prevention of cancer. In one embodiment, the invention provides a method of treating or preventing cancer, comprising administering to a patient in need thereof an immune checkpoint modulator together with a compound of Formula (I):

Formula (I)

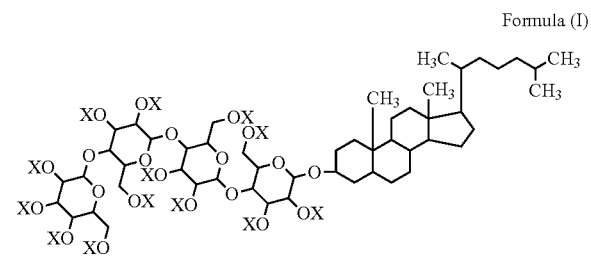

wherein X is $SO_3M$ or H, wherein M is any pharmaceutically acceptable cation; and wherein at least 70% of the X groups is $SO_3M$.

19 Claims, 20 Drawing Sheets

(56) References Cited

OTHER PUBLICATIONS

Brennan et al., "Heparan sulfate mimetic PG545-mediated antilymphoma effects require TLR-9 dependent NK cell activation," *The Journal of Clinical Investigation* 126(1):207-219, Jan. 2016 and supplemental data (6 pages).

Chen, "Immune checkpoint inhibitors for nonsmall cell lung cancer treatment," *Journal of the Chinese Medical Association* 80(1):7-14, Jan. 2017.

Dredge et al., "The PG500 series: novel heparan sulfate mimetics as potent angiogenesis and heparanase inhibitors for cancer therapy," *Investigational New Drugs* 28(3):276-283, May 2009 and supplemental data (1 page).

Ferro et al., "Discovery of PG545: A Highly Potent and Simultaneous Inhibitor of Angiogenesis, Tumor Growth, and Metastasis," *Journal of Medical Chemistry* 55(8):3804-3813, 2012.

Franklin et al., "Immunotherapy in melanoma: Recent advances and future directions," *European Journal of Surgical Oncology* 43(3):604-611, Mar. 2017.

Hammond et al., "PG545, a Heparan Sulfate Mimetic, Reduces Heparanase Expression In Vivo, Blocks Spontaneous Metastases and Enhances Overall Survival in the 4T1 Breast Carcinoma Model," *PLoS One* 7(12):1-11, Dec. 2012 and supplemental data (1 page).

Hammond et al., "Mechanisms of heparanase inhibition by the heparan sulfate mimetic PG545 and three structural analogues," *FEBS Open Bio* 3(1):346-351, 2013.

Jung et al., "The heparan sulfate mimetic PG545 interferes with Wnt/β-catenin signaling and significantly suppresses pancreatic tumorigenesis alone or in combination with gemcitabine," *Oncotarget* 6(7):4992-5004, Jan. 2015 and supplemental data (12 pages).

Le et al., "PD-1 Blockade in Tumors with Mismatch-Repair Deficiency," *The New England Journal of Medicine* 372(26):2509-2520, 2015.

Mennitto et al., "Nivolumab in the treatment of advanced renal cell carcinoma: clinical trial evidence and experience," *Therapeutic Advances in Urology* 8(5):319-326, 2016.

Ostapoff et al., "PG545, an Angiogenesis and Heparanase Inhibitor, Reduces Primary Tumor Growth and Metastasis in Experimental Pancreatic Cancer," *Molecular Cancer Therapeutics* 12(7):1190-1201, Jul. 2013.

Restifo et al., "Acquired resistance to immunotherapy and future challenges," *Nature Reviews Cancer* 16(2):121-126, Jan. 2016.

Spranger et al.., "Tumor and Host Factors Controlling Antitumor Immunity and Efficacy of Cancer Immunotherapy," *Advances in Immunology* 130:75-93, 2016.

Topalian et al., "Safe, Activity, and Immune Correlates of Anti-PD-1 Antibody in Cancer," *The New England Journal of Medicine* 366(26):2443-2454, Jun. 2012.

U.S. Food and Drug Administration, "Nivolumab (Opdivo) for Hodgkin Lymphoma," May 2016, https://www. https://www.fda.gov/drugs/resources-information-approved-drugs/nivolumab-opdivo-hodgkin-lymphoma, downloaded. Jul. 1, 2020.

Winterhoff et al., "PG545 enhances anti-cancer activity of chemotherapy in ovarian models and increases surrogate biomarkers such as VEGF in preclinical and clinical plasma samples," *European Journal of Cancer* 51(7):879-892, May 2015 and supplemental data (9 pages).

Woo et al., "The STING pathway and the T cell-inflamed tumor microenvironment," *Trends in Immunology* 36(4):250-256, Apr. 2015.

Zhang et al., "Myeloid cells are required for PD-1/PD-L1 checkpoint activation and the establishment of an immunosuppressive environment in pancreatic cancer," *Gut* 66(1):124-136, Jan. 2017.

Zhu et al., "CSF1/CSF1R Blockade Reprograms Tumor-Infiltrating Macrophages and Improves Response to T-cell Checkpoint Immunotherapy in Pancreatic Cancer Models," *Cancer Research* 74(18):5057-5069, Sep. 2014.

* cited by examiner

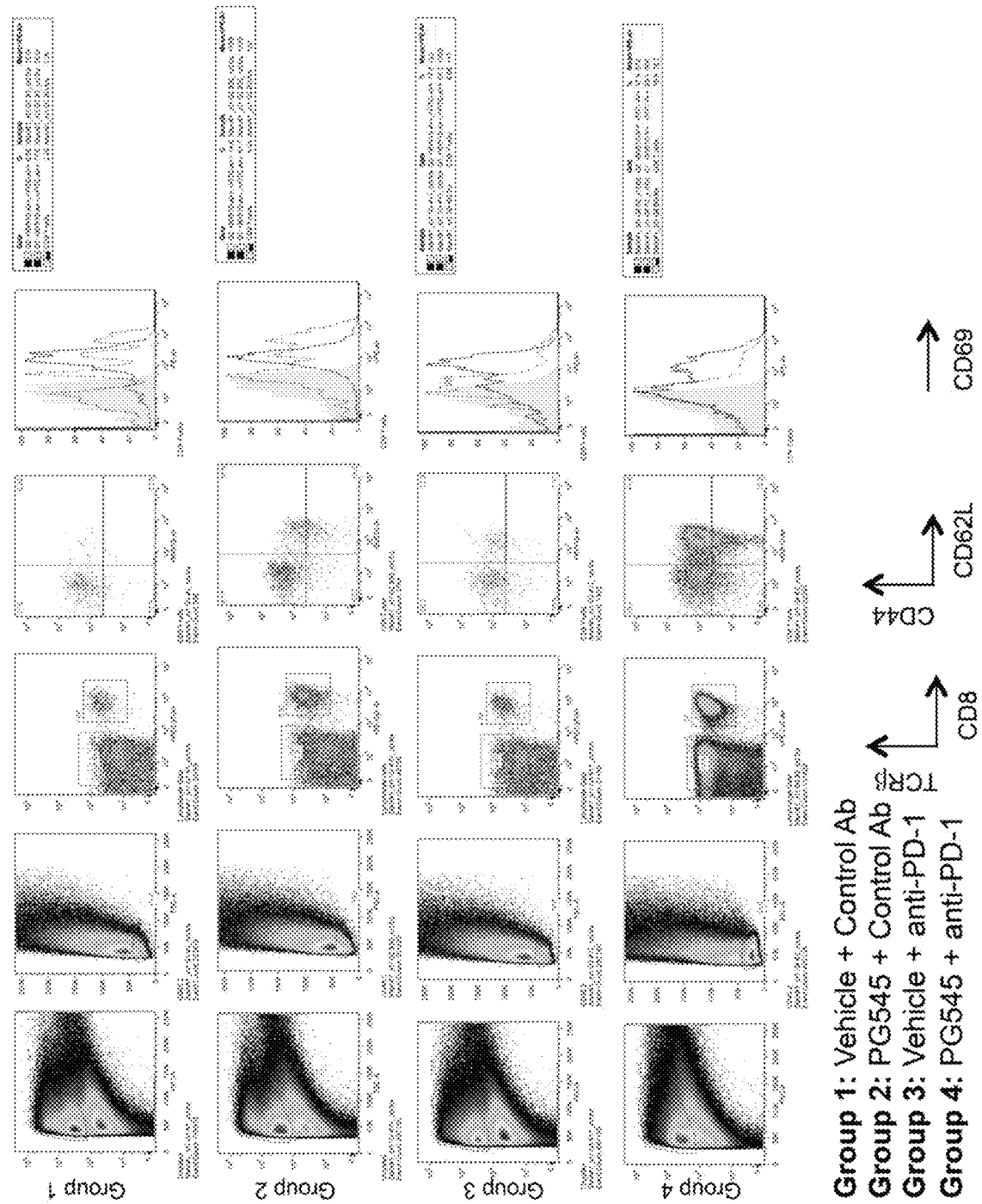

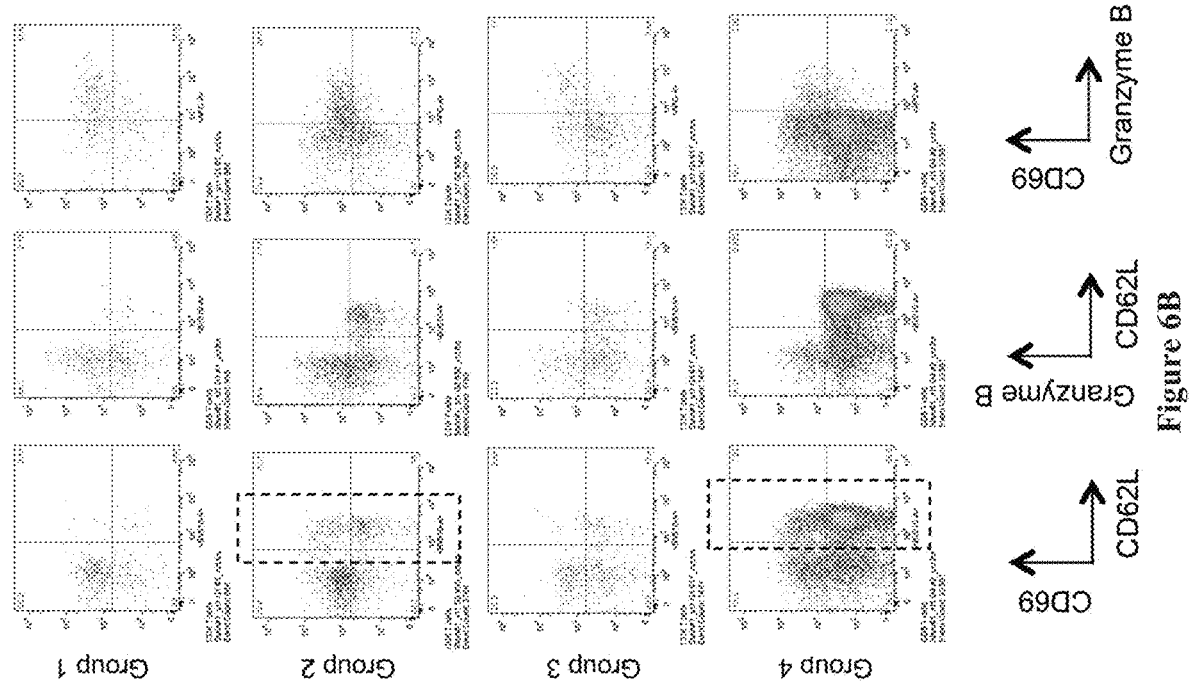

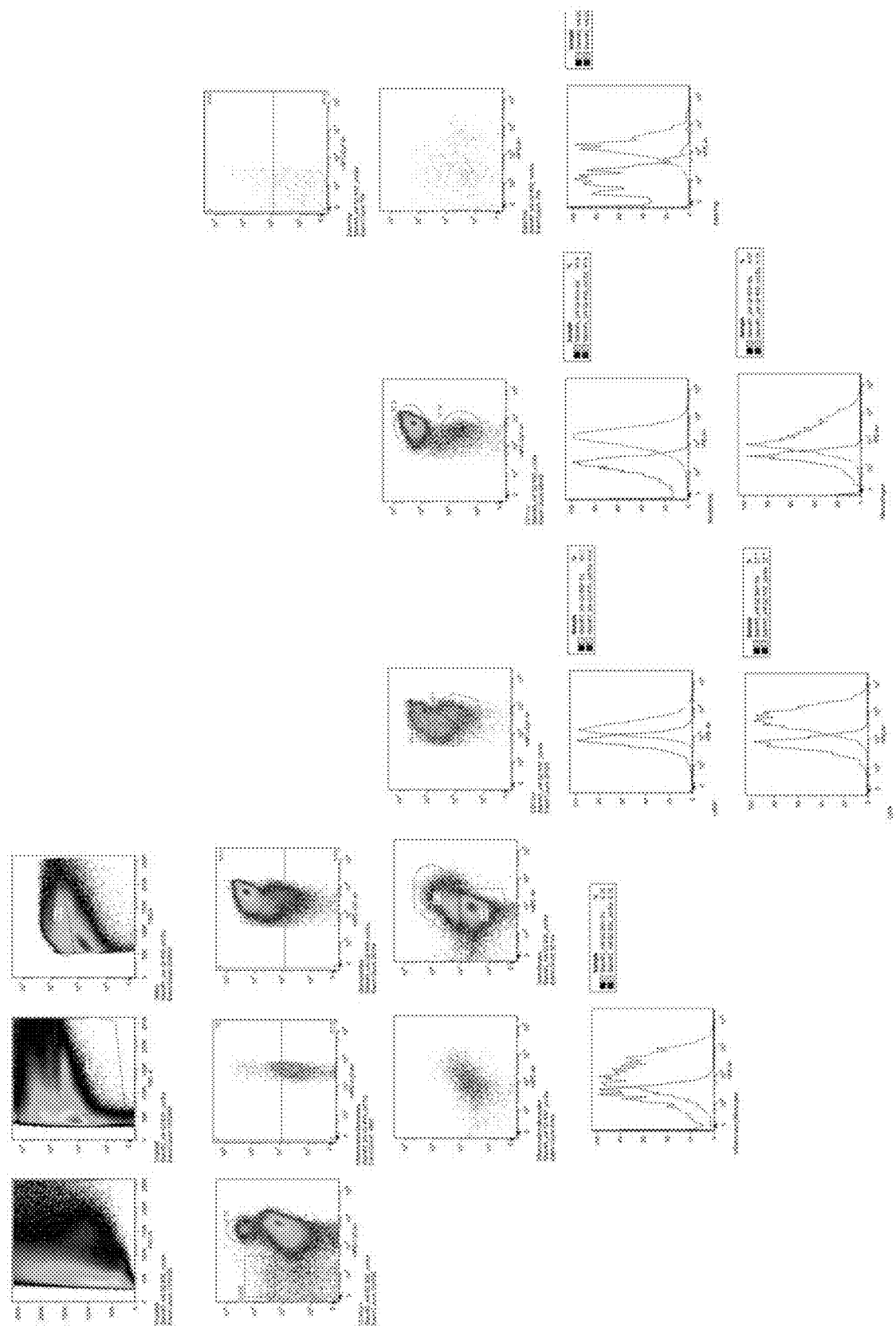
Labels are as shown in Figure 13A    Figure 13B

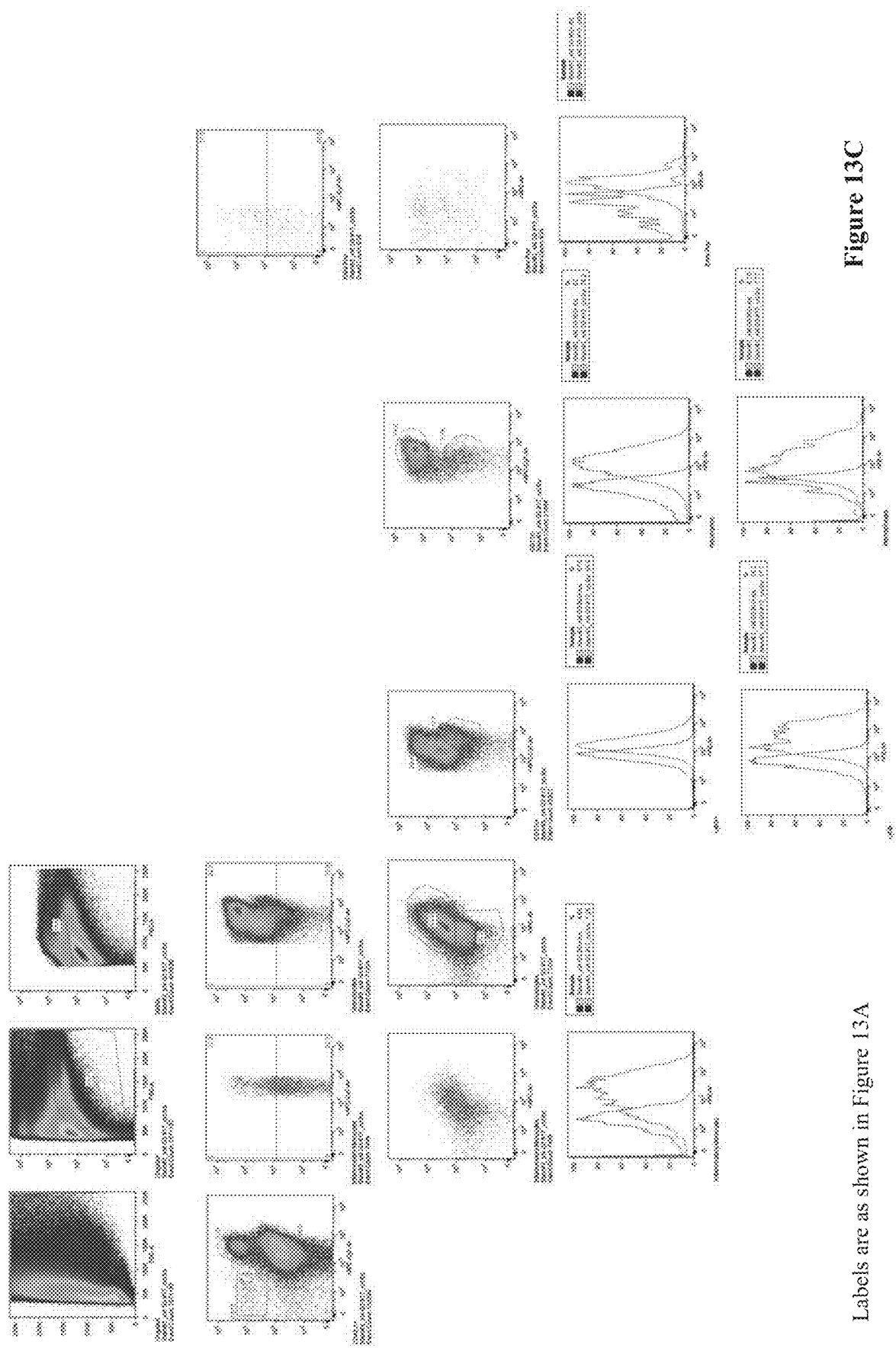

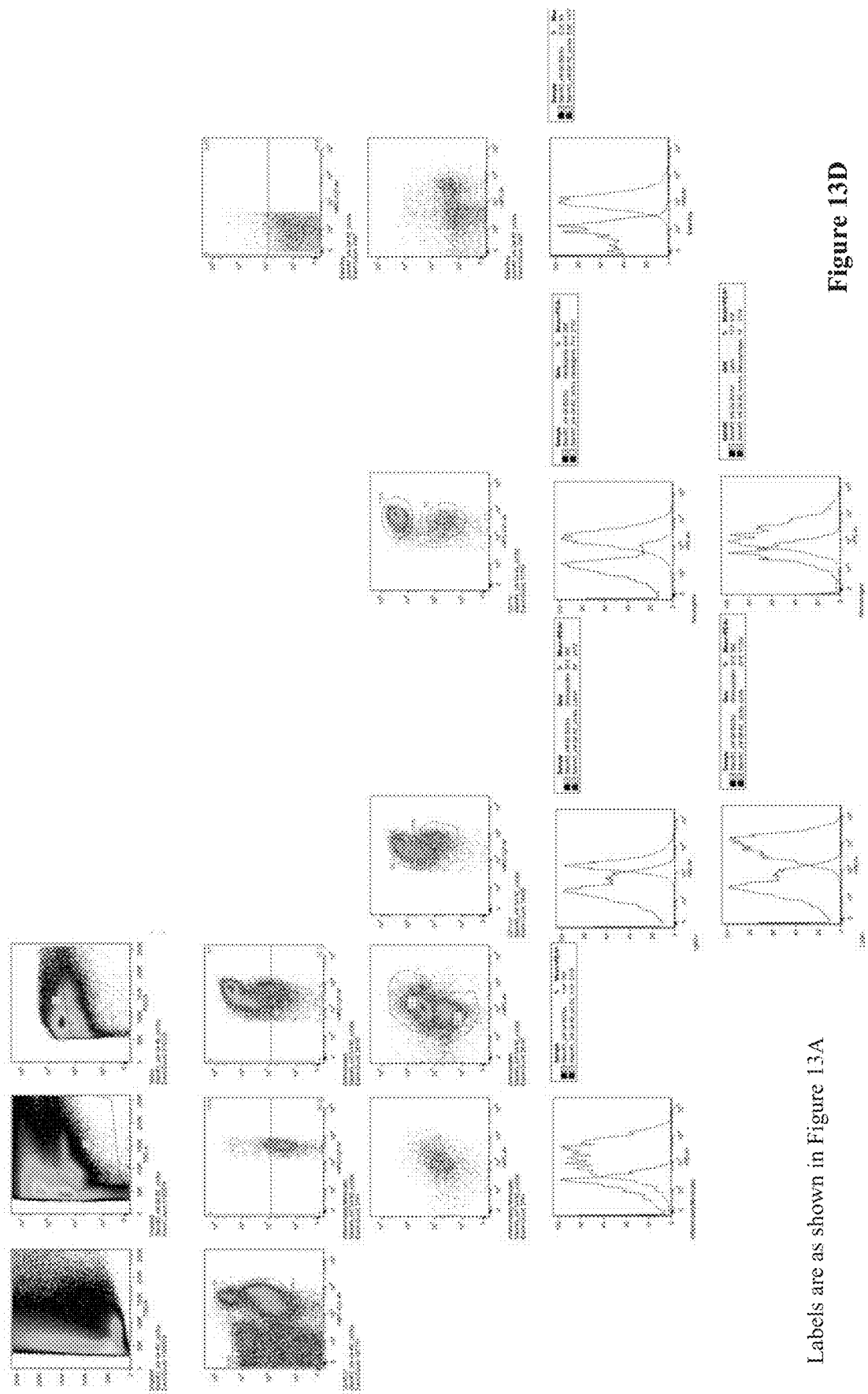

COMPOSITION AND USES THEREOF

CROSS REFERENCE TO RELATED APPLICATIONS

This application is a continuation-in-part of International Application No. PCT/AU2017/051402, filed on Dec. 15, 2017, which claims priority to Australian Application No. 2016905199, filed on Dec. 15, 2016, both of which are incorporated herein by reference.

TECHNICAL FIELD

The present invention relates, inter alia, to methods and uses for the prevention or treatment of cancer, and to compositions, combinations and kits for the treatment or prevention of cancer.

BACKGROUND ART

It will be clearly understood that, if a prior art publication is referred to herein, this reference does not constitute an admission that the publication forms part of the common general knowledge in the art in Australia or in any other country.

The immune system can be effective in combating malignant tumour cells that arise in the human body. If malignant tumour cells can evade the immune system they can proliferate and spread, developing into life threatening cancer. Numerous cancers have developed the capability to evade the immune system, many of them very serious diseases that affect the health and reduce the life expectancy of a large number of people worldwide.

Success has been achieved in the treatment of cancer using therapeutics that specifically target the processes employed by cancer cells to evade the immune system. One key process involves checkpoint targets (such as checkpoint receptors and checkpoint ligands). In healthy tissue, checkpoint targets are important in preventing over stimulation of the immune system that could otherwise lead to autoimmune diseases. However, many types of cancer cells interact with one or more of these checkpoint targets thus allowing them to lessen or inactivate an immune response. Checkpoint modulators are therapeutics which modulate checkpoint targets on the surface of immune cells, preventing cancer cells from selectively engaging these checkpoint targets to inactivate the immune cells.

Pharmaceuticals that target the checkpoint receptors PD-1 and CTLA-4, for example, have recently been approved to treat a variety of cancers. Nivolumab and pembrolizumab are inhibitors of PD-1 and ipilimumab inhibits CTLA-4. The cancers for which these agents have been approved include melanoma (ipilimumab, nivolumab, pembrolizumab; Franklin 2016), non-small cell lung cancer (NSCLC) (nivolumab, pembrolizumab; Chen 2016), renal cell cancer (RCC) (nivolumab; Mennitto 2016) and Hodgkin lymphoma (nivolumab; US FDA 2016). However, even in these cancers there are numerous patients who derive limited, or no benefit from treatment.

PG545 is a cholestanol-sulfotetrasaccharide conjugated small molecule compound, especially for the treatment of cancer. PG545 has been described as a heparanase inhibitor (Dredge et al, 2010, Hammond et al, 2013) but also possesses immunomodulatory properties. Use of this compound has been demonstrated to lead to a depletion of immunosuppressive pro-cancer immune cells such as tumour-associated macrophages (TAMs) and myeloid-derived suppressor cells (MDSCs) within the tumour microenvironment (TME) as evidenced by preclinical models of pancreatic cancer (Ostapoff et al, 2013) and a chemically-induced model of skin cancer (Boyango et al, 2014).

However, PG545 also drives a strong immunostimulatory activity on the dendritic cell (DC), another myeloid-derived cell, via the MyD88-dependant toll-like receptor 9 (TLR9) pathway and the subsequent activation of natural killer (NK) cells (Brennan et al, 2016). The authors also found that the immunostimulatory effect of PG545 was reproduced in heparanase knockout mice but that another heparanase inhibitor, muparfostat (PI-88), did not have this activity profile in normal mice (unpublished data). Taken together these results demonstrate that PG545's effect on DCs is heparanase-independent. Moreover, PG545's effect on DCs led to potent activation of NK cells but not T cells (Brennan et al, 2016). As illustrated in Brennan et al, 2016, administration of PG545 alone does not activate T cells in naïve mice (see FIG. 3C), nor in mice bearing A20 lymphoma tumours (see FIGS. 2C and E of the Supplementary Material). Thus, the immunomodulatory activity of PG545 has not shown any interaction or impact on T cells or adaptive immunity.

SUMMARY

The present invention is directed, inter alia, to methods, compositions or kits which may improve the immune response to cancer cells, or which may provide the consumer with a useful or commercial choice.

With the foregoing in view, the present invention in some forms resides broadly in methods, uses, combinations, kits and compositions for treating or preventing cancer.

In a first aspect, the present invention provides a method of treating or preventing cancer, comprising administering to a patient in need thereof an immune checkpoint modulator together with a compound of Formula (I):

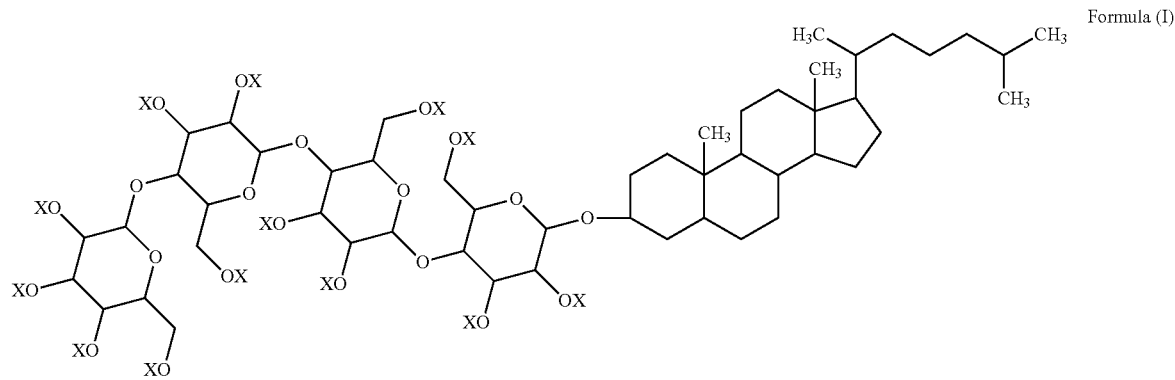

wherein X is SO₃M or H, wherein M is any pharmaceutically acceptable cation; and wherein at least 70% of the X groups is SO₃M.

Advantageously, it has been found that a compound of Formula (I) and an immune checkpoint modulator, especially a T cell immune checkpoint inhibitor, have a synergistic effect to accumulate T cells in tumours. This effect is especially surprising, given that a compound of Formula (I) has been shown to have no interaction or impact on T cells (Brennan et al, 2016). Furthermore, in some studies the immune checkpoint modulator when administered alone has been shown to provide a limited effect on the accumulation of T cells in tumours (see Spranger 2016 for example). This synergistic effect is believed to enable a patient's immune system to provide an enhanced immune response specifically against cancer cells.

In one embodiment, at least 9 of the X groups in the compound of Formula (I) is SO₃M. In another embodiment, at least 10 of the X groups in the compound of Formula (I) is SO₃M; especially at least 11 of the X groups in the compound of Formula (I) is SO₃M; more especially at least 12 of the X groups in the compound of Formula (I) is SO₃M; most especially 13 or all of the X groups in the compound of Formula (I) is SO₃M. In one embodiment, at least 75% of the X groups is SO₃M; especially at least 80% of the X groups is SO₃M; more especially at least 90% of the X groups is SO₃M; most especially 100% of the X groups is SO₃M.

In the compound of Formula (I), M may be any pharmaceutically acceptable cation. Exemplary cations include sodium, calcium, potassium, magnesium or ammonium; especially sodium or potassium; more especially sodium.

In one embodiment, the compound of Formula (I) may be a compound of Formula (II):

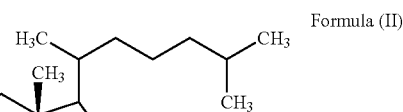

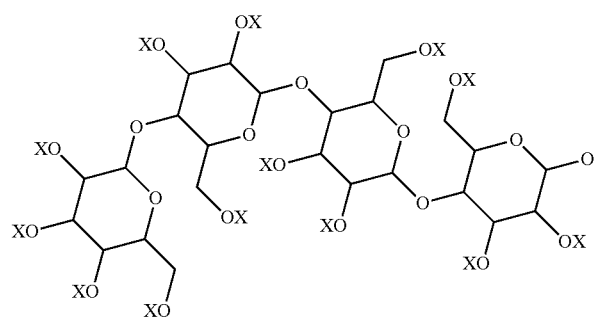

In another embodiment, the compound of Formula (I) may be a compound of Formula (III):

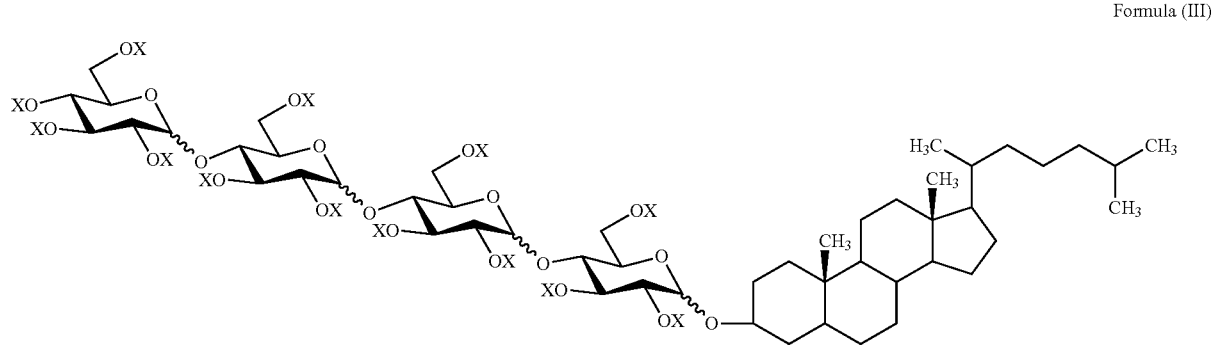

In another embodiment, the compound of Formula (I) may be a compound of Formula (IV):
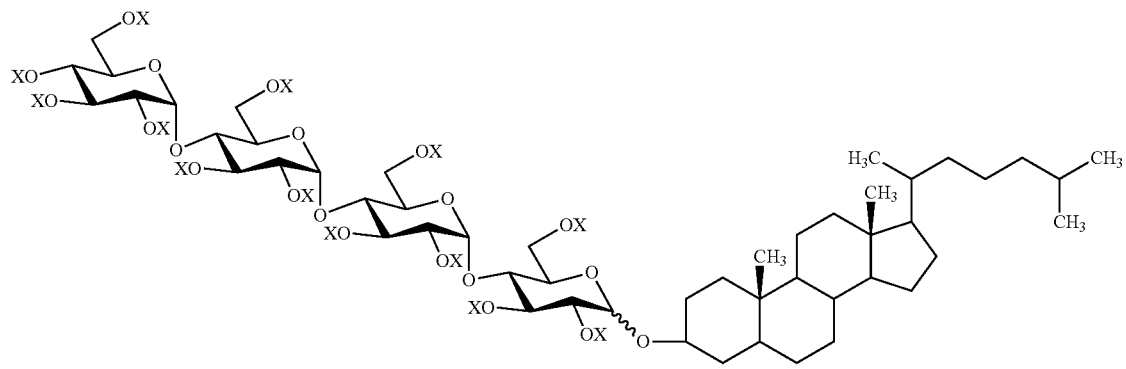
Formula (IV)
In another embodiment, the compound of Formula (I) may be a compound of Formula (V):
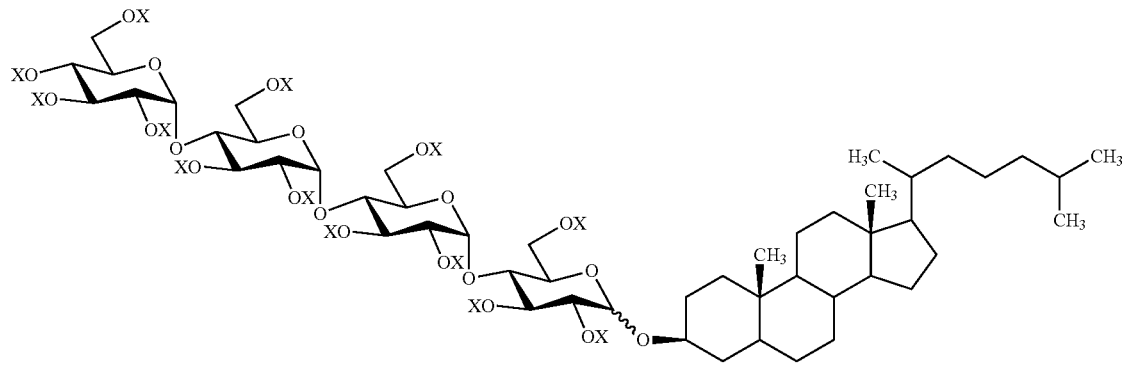
Formula (V)
In another embodiment, the compound of Formula (I) may be a compound of Formula (VI):
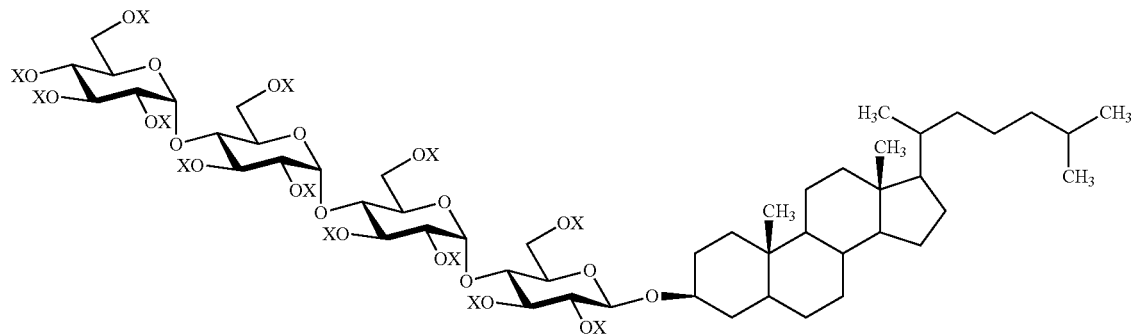
Formula (VI)

In another embodiment, the compound of Formula (I) may be a compound of Formula (VII):

Formula (VII)

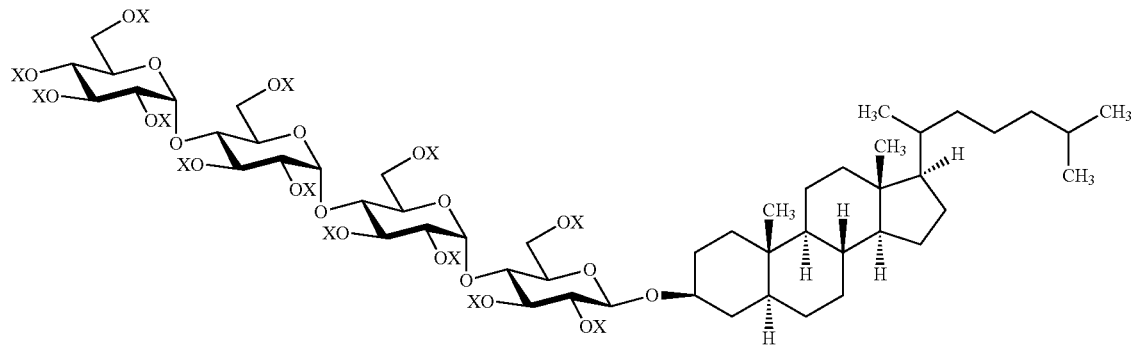

The compounds of Formulae (II) to (VII) possess asymmetric centres. These compounds may be in substantially pure isomeric form at one or more of said centres, for example greater than about 90% enantiomeric excess (ee) or diasteromeric excess (de), such as greater than 95% ee or de, or greater than 97% ee or de, or greater than 99% ee or de. Such isomers may be prepared by asymmetric synthesis, for example using chiral starting materials or intermediates, or by chiral resolution.

If the compound of Formula (I) is a compound of Formula (VII), and X is $SO_3Na$, then the compound is PG545. In one embodiment, the compound of Formula (I) is PG545. PG545 is 3β,5α-cholestanyl 2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside, and is described in WO2009/049370.

In one embodiment, the immune checkpoint modulator is an immune checkpoint inhibitor or an immune checkpoint activator; especially an immune checkpoint inhibitor. In another embodiment, the immune checkpoint modulator targets one or more of a T cell, an Antigen-Presenting Cell (APC)/tumour cell, a Natural Killer (NK) cell, a Natural Killer T cell (NKT), a Gamma Delta T cell, an invariant T cell, or an invariant Natural Killer T cell (NKT). The immune checkpoint modulator especially targets a T cell; and is especially a T cell immune checkpoint inhibitor. The immune checkpoint modulator may target a CD8 T cell, especially an effector memory CD8 T cell or a central memory CD8 T cell. The immune checkpoint modulator may target a CD4 T cell.

The immune checkpoint modulator may target one or more of: CTLA-4, PD-1, PD-L1, LAG3, B7-H3, B7-H4, TIM3, Galectin9, BTLA, HVEM, A2aR, VISTA, KIR, TIGIT, IDO, CD47, CD28, ICOS, CD137 (4-1BB), CD137L, CD40, CD40L, OX40, OX40L, GITR and CD27. The immune checkpoint modulator may target one or more of: CTLA-4, PD-1, LAG3, TIM3, BTLA, A2aR, CD28, ICOS, CD137 (4-1BB), CD40L, OX40, GITR and CD27. The immune checkpoint modulator may target one or more of PD-1, CTLA-4 or PD-L1. The immune checkpoint modulator may target PD-1. The immune checkpoint modulator may be a PD-1 inhibitor.

The immune checkpoint modulator may be one or more of: Ipilimumab, Tremelimumab, Nivolumab, Pembrolizumab, Pidilizumab, Atezolizumab, Avelumab, Durvalumab, Enoblituzumab, Lirilumab, Epacadostat, Indoximod, Urelumab, Utomilumab, Lucatumumab, Dacetuzumab, Oxelumab, and Varlilumab. The immune checkpoint modulator may especially be Nivolumab, Pembrolizumab or Pidilizumab.

Exemplary immune checkpoint targets, cell types and agents are provided in Table 1.

TABLE 1

Immune Checkpoint Targets and Agents

| Target | Cell Type | Inhibitory/ Activating | Agent | Synonym |
|---|---|---|---|---|
| CTLA-4 | T cell | Inhibitory | Ipilimumab | — |
| | T cell | Inhibitory | Tremelimumab | CP-675,206 |
| PD-1 | T cell | Inhibitory | Nivolumab | MDX-1106 (BMS-936558) |
| | T cell | Inhibitory | Pembrolizumab | MK-3475 (lambrolizumab) |
| | T cell | Inhibitory | Pidilizumab | CT-011 |
| | T cell | Inhibitory | | AMP-224 |
| PD-L1 | APC/tumour cell | Inhibitory | Atezolizumab | MDPL3280 (RG7446) |
| | APC/tumour cell | Inhibitory | Avelumab | MSB0010718C |
| | APC/tumour cell | Inhibitory | Durvalumab | MEDI-4736 |
| | APC/tumour cell | Inhibitory | N/A | MDX-1105 (BMS-936559) |
| LAG3 | T cell | Inhibitory | N/A | IMP321 |
| | T cell | Inhibitory | N/A | IMP701 |
| | T cell | Inhibitory | N/A | LAG525 |
| B7-H3 | APC/tumour cell | Inhibitory | Enoblituzumab | MGA271 |
| B7-H4 | APC/tumour cell | Inhibitory | N/A | Developed by AstraZeneca |
| TIM3 | T cell | Inhibitory | N/A | MGB453 |
| | T cell | Inhibitory | N/A | CA-327 |
| Galectin9 | APC/tumour cell | Inhibitory | N/A | Developed by GlycoMimetics |
| BTLA | T cell | Inhibitory | N/A | |
| HVEM | APC/tumour cell | Inhibitory | N/A | |
| A2aR | T cell | Inhibitory | N/A | CPI-444 |
| VISTA | APC/tumour cell | Inhibitory | N/A | JNJ 61610588 |
| | APC/tumour cell | Inhibitory | N/A | CA-170 |
| KIR | NK cell | Inhibitory | Lirilumab | BMS-986015 (IPH2102) |
| TIGIT | NK cell | Inhibitory | N/A | MTIG7192A, RG6058 |

TABLE 1-continued

Immune Checkpoint Targets and Agents

| Target | Cell Type | Inhibitory/Activating | Agent | Synonym |
|---|---|---|---|---|
| IDO | APC/tumour cell | Inhibitory | Epacadostat | INCB024360 |
| | APC/tumour cell | Inhibitory | Indoximod | NLG-8189 |
| CD47 | APC/tumour cell | Inhibitory | N/A | Hu5F9-G4 |
| CD28 | T cell | Activating | N/A | TGN1412 |
| ICOS | T cell | Activating | N/A | JTX-2011 |
| CD137 (4-1BB) | T cell | Activating | Urelumab | BMS-663513 |
| | T cell | Activating | Utomilumab | PF-05082566 (PF-2566) |
| CD137L | APC/tumour cell | Activating | N/A | |
| CD40 | APC/tumour cell | Activating | N/A | SEA-CD40 |
| | APC/tumour cell | Activating | Lucatumumab | HCD120 |
| | APC/tumour cell | Activating | Dacetuzumab | SGN-40, huS2C6 |
| CD40L | T cell | Activating | N/A | |
| OX40 | T cell | Activating | N/A | Anti-OX40 mAb (9B12) |
| OX40L | APC/tumour cell | Activating | Oxelumab | |
| GITR | T cell | Activating | N/A | TRX518, INCAGN1876 |
| | T cell | Activating | N/A | MK-4166 |
| CD27 | T cell | Activating | Varlilumab | CDX-1127 |

APC—Antigen-presenting cell
NK—Natural Killer cell
N/A—Not available

The patient may be a mammal, especially a human. However, the patient may be a primate or a veterinary patient, such as a dog, cat or horse.

The cancer may be a malignant or a benign cancer, especially a malignant cancer. The cancer may be a solid tumour or a haematological tumour. The haematological tumour may be a haematological malignancy such as, for example, lymphoma, myeloma or leukemia. The solid tumour may be selected from the group consisting of: melanoma, colon cancer, breast cancer, prostate cancer, liver cancer, lung cancer (including non-small cell, small cell or mesothelioma), head and neck cancer, skin cancer, renal cancer, pancreatic cancer, oesophageal cancer, cholangiocarcinoma, gastric cancer, urothelial or bladder cancer, sarcoma, uterine cancer, endometrial cancer, ovarian cancer, cervical cancer and brain cancer (including glioma and astrocytoma). The cancer may be breast cancer.

The cancer may be a tumour enriched with T cells. In another embodiment, the cancer may be a tumour including substantially no T cells, or a tumour resistant to accumulation of T cells. A tumour including substantially no T cells, or a tumour resistant to accumulation or infiltration of T cells is sometimes called a "cold" or "non-inflamed" tumour, and such terms would be known to a skilled person (see Spranger 2016, Woo 2015, for example). It is believed that the compound of Formula (I) and the immune checkpoint modulator may inflame or convert such a "cold" tumour into a "hot" or "inflamed" tumour which is enriched with T cells, thereby improving the immune response to the tumour.

As a result of administration of the immune checkpoint modulator and the compound of Formula (I), cancer may be more effectively treated or prevented, and/or a medically beneficial effect on a tumour may be provided. Administration of the immune checkpoint modulator and the compound of Formula (I) may initiate, enable, increase, enhance or prolong the activity of immune cells against the cancer and/or may provide an anti-tumour adaptive immune response.

Administration of the immune checkpoint modulator and the compound of Formula (I) may increase the number of immune cells accumulating in the tumour. Administration of the immune checkpoint modulator and the compound of Formula (I) may lead to accumulation of lymphocytes in a tumour; especially T cells; more especially Effector Memory $CD8^+$ T cells, Central Memory $CD8^+$ T cells and $CD4^+$ T cells.

As used herein, the terms "treatment" (or "treating") and "prevention" (or "preventing") are to be considered in their broadest contexts. For example, the term "treatment" does not necessarily imply that a patient is treated until full recovery. The term "treatment" includes amelioration of the symptoms of a disease or condition, or reducing the severity of a disease or condition. Similarly, "prevention" does not necessarily imply that a subject will never contract a disease or condition. "Prevention" may be considered as reducing the likelihood of onset of a disease or condition, or preventing or otherwise reducing the risk of developing a disease or condition.

The method may include administering an effective amount of the immune checkpoint modulator and/or an effective amount of the compound of Formula (I). An "effective amount" of a compound of Formula (I) means an amount necessary to at least partly attain the desired response, or to delay the onset or progression of the cancer. The amount may vary depending on factors such as: the health and physical condition of the individual to whom the compound is administered, the taxonomic group of the individual to whom the compound is administered, the extent of treatment/prevention desired, the formulation of the composition, and the assessment of the medical situation. It is expected that the "effective amount" will fall within a broad range that can be determined through routine trials. An effective amount in relation to a human patient, for example, may lie in the range of about 0.1 ng per kg of body weight to 1 g per kg of body weight per dosage, or in the range of about 100 ng to 100 mg per kg of body weight per dosage. Dosage regimes may be adjusted to provide the optimum therapeutic response. For example, several doses may be administered daily, bi-weekly or weekly, or at other suitable time intervals, or the dose may be proportionally reduced as indicated by the circumstances. Decisions on dosage and the like would be within the skill of the medical practitioner or veterinarian responsible for the care of the patient. In one embodiment, the compound of Formula (I) may be administered bi-weekly, weekly, once every two weeks, once every three weeks or once every month. In another embodiment, the immune checkpoint modulator may be administered bi-weekly, weekly, once every two weeks, once every three weeks or once every month.

In one embodiment the compound of Formula (I) may be administered at a dose of less than 100 mg per week, especially less than 50 mg per week. The compound of Formula (I) may be administered at a dose of from 1 to 100 mg per week, especially from 1 to 50 mg per week, more especially from 5 to 45 mg per week or from 10 to 40 mg per week or from 15 to 35 mg per week or from 20 to 30 mg per week, most especially about 25 mg per week. In another embodiment, the immune checkpoint modulator (especially immune checkpoint inhibitor) may be administered at a dose of from 1 to 1000 mg per week or per two weeks; especially from 1 to 500 mg per week or per two weeks, or from 50 to 450 mg per week or per two weeks, or from 100 to 400 mg per week or per two weeks, or from 150 to 350 mg per week or per two weeks, or from 200 to 300 mg per week or per two weeks; more especially from 220 to 260 mg per week or per two weeks, or about 240 mg per week or per two weeks; most especially about 240 mg per two weeks.

The compound of Formula (I) and the immune checkpoint modulator may be administered sequentially, simultaneously or substantially simultaneously. The compound of Formula (I) may be administered prior to, or after, the immune checkpoint modulator. Either or both of the compound of Formula (I) and the immune checkpoint modulator may be administered as part of a treatment regime or cyclical dosage. The immune checkpoint modulator and the compound of Formula (I) may accumulate in the patient over time, and consequently the immune checkpoint modulator and the compound of Formula (I) may be administered hours or days apart yet still act synergistically.

While it is possible that the compound of Formula (I) and the immune checkpoint modulator may be administered as neat chemicals, they may be administered as part of a pharmaceutical composition which includes a carrier or excipient. The compound of Formula (I) and the immune checkpoint modulator may be provided together in a single pharmaceutical composition. Alternatively, the compound of Formula (I) and the immune checkpoint modulator may be provided in separate pharmaceutical compositions. If the compound of Formula (I) and the immune checkpoint modulator are to be administered at different times, or at varying dosages, it may be advantageous to provide the compound of Formula (I) and the immune checkpoint modulator in separate pharmaceutical compositions.

Any said pharmaceutical composition may comprise the active agent (i.e. a compound of Formula (I) and/or the immune checkpoint modulator) and a pharmaceutically acceptable carrier or excipient. Any pharmaceutically acceptable carrier(s) or excipient(s) must be acceptable in the sense of being compatible with the other components in the composition and not being deleterious to the patient.

The type of pharmaceutical composition may depend upon the Absorption, Distribution, Metabolism and Excretion (ADME) profile of the active agent. For example, it may be most appropriate for compounds of Formula (I) and/or immune checkpoint inhibitors to be administered parenterally, especially intravenously, and consequently the pharmaceutical composition may be formulated for parenteral or intravenous administration. Nevertheless, if possible the pharmaceutical composition may include those suitable for oral or rectal administration, or for administration by non-intravenous routes.

Parenteral administration may include administration by one or more of the following routes: intravenously, intrathecally, cutaneously, subcutaneously, nasally, intramuscularly, intraocularly, transepithelially, vaginally, intraperitoneally and topically. Topical administration includes buccal, sub-lingual, dermal, ocular, rectal, nasal, as well as administration by inhalation or by aerosol means. For intravenous, cutaneous or subcutaneous injection, or injection at a site where treatment is desired, the active agent may be in the form of a parenterally acceptable aqueous solution which is pyrogen-free and has suitable pH, isotonicity and stability. Those of skill in the art would be able to prepare suitable solutions.

The nature of the pharmaceutical composition and the carrier or excipient will depend on the route of administration and the nature of the condition and the patient being treated. It is believed that the choice of a particular carrier, excipient or delivery system, and route of administration could be readily determined by a person skilled in the art. In some circumstances it may be necessary to protect the active agent by means known in the art, for example, by micro encapsulation. The route of administration should also be chosen such that the active agent reaches its site of action. The pharmaceutical composition may include any suitable effective amount of the active agent commensurate with the intended dosage range to be employed.

The pharmaceutical composition may be in the form of a solid (including tablets, filled capsules, powders, cachets, capsules, troches, suppositories, wafers, dispersible granules and pessaries), or a liquid (including solutions, suspensions, syrups, emulsions, colloids, elixirs, creams, gels and foams). In one embodiment, the pharmaceutical composition may be in the form of a sterile injectable solution for parenteral use.

The pharmaceutically acceptable carrier or excipient may be either a solid or a liquid. The carrier or excipient may act as a diluent, buffer, stabiliser, isotonicising agent, flavouring agent, anti-oxidant, solubilizer, lubricant, suspending agent, binder, preservative, tablet disintegrating agent or an encapsulating material. Suitable carriers and excipients would be known to a skilled person. With regard to buffers, aqueous compositions may include buffers for maintaining the composition at close to physiological pH or at least within a range of about pH 6.0 to 9.0.

If the pharmaceutical composition is a powder, the active agent and a carrier or excipient may both be finely divided powders which are mixed together.

If the pharmaceutical composition is a tablet, the active component may be mixed with a suitable amount of a carrier or excipient which has the necessary binding capacity before compaction into a tablet of the desired shape and size.

Powders or tablets may include any suitable amount of the active agent, and exemplary amounts of the active agent in the powder or tablet may range from about five or ten percent to about seventy percent. Exemplary carriers or excipients for powders and tablets may include, for example, magnesium carbonate, talc, sugar, lactose, pectin, dextrin, starch, gelatin, tragacanth, methylcellulose, a low melting wax, cocoa butter and the like.

Liquid form preparations may include, for example, water, saline, water-dextrose, water-propylene glycol, petroleum, or oil (including animal, vegetable mineral or synthetic oil) solutions. For example, parenteral injection liquid preparations may be formulated as solutions in aqueous polyethylene glycol solution. Such liquid form preparations may contain at least 0.1 wt % of the active compound.

Liquid pharmaceutical compositions may be formulated in unit dose form. For example, the compositions may be presented in ampoules, pre-filled syringes, small volume infusion or in multi-dose containers. Such compositions may include a preservative. The compositions may also include formulatory agents such as suspending, stabilising and/or dispersing agents. The composition may also be in powder form for constitution with a suitable vehicle (such as sterile water) before use. Liquid carriers and excipients may include colorants, flavours, stabilizers, buffers, artificial and natural sweeteners, dispersants, thickeners, solubilizing agents, suspending agents and the like.

Aqueous solutions for oral use may be prepared by dissolving the active agent in water and adding colourants, thickeners, flavours, and stabilizing agents, as necessary. Aqueous suspensions for oral use may be prepared by dispersing the active agent in water with viscous material, such as natural or synthetic gums, resins, methyl cellulose or other suspending agents.

For topical administration to the epidermis the compounds may be formulated as an ointment, cream or lotion, or as a transdermal patch.

The compositions may also be administered by inhalation in the form of an aerosol spray from a pressurised dispenser or container, which contains a propellant such as carbon dioxide gas, dichlorodifluoromethane, nitrogen, propane or other suitable gas or gas combination. The pharmaceutical composition may be in a form suitable for administration by inhalation or insufflation.

The pharmaceutical composition may be adapted to provide sustained release of the active agent.

The pharmaceutical composition may be in unit dosage form. In such form, the pharmaceutical composition may be prepared as unit doses containing appropriate quantities of the active agent. The unit dosage form may be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical composition may also include at least one further active ingredient, in addition to the compound of Formula (I) and/or the immune checkpoint modulator. Such ingredients may have efficacy as anti-cancer, anti-angiogenic, anti-metastatic, anti-inflammatory, anti-coagulant, antimicrobial or anti-thrombotic agents, and agents effective against elevated blood triglyceride levels and cardiovascular disease. However, the pharmaceutical composition may include any suitable further active ingredient.

In a second aspect, the present invention provides a use of a compound of Formula (I) in the manufacture of a medicament for the treatment or prevention of cancer, wherein the compound of Formula (I) is:

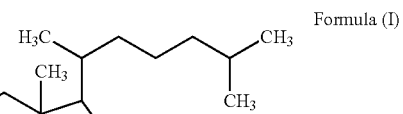

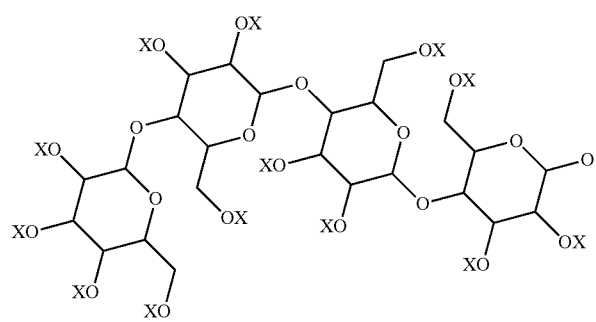

Formula (I)

wherein X is SO₃M or H, wherein M is any pharmaceutically acceptable cation; and wherein at least 70% of the X groups is SO₃M;
and wherein the medicament is formulated for administration with an immune checkpoint modulator.

In a third aspect, the present invention provides a use of an immune checkpoint modulator in the manufacture of a medicament for the treatment or prevention of cancer,
wherein the medicament is formulated for administration with a compound of Formula (I):

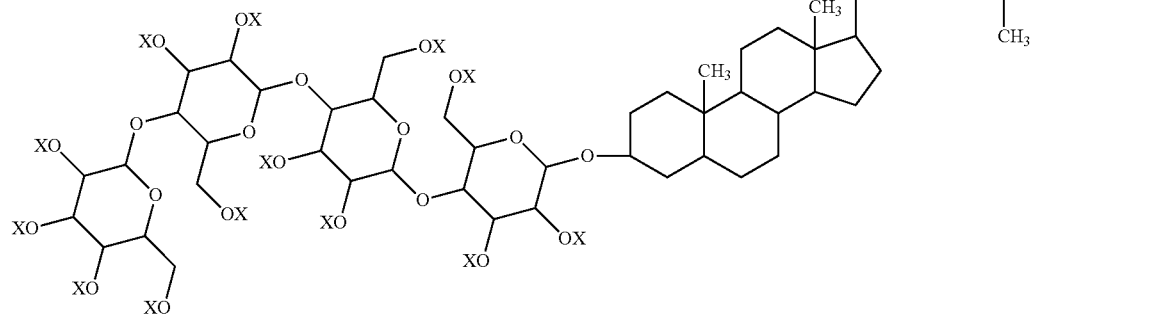

wherein X is SO₃M or H, wherein M is any pharmaceutically acceptable cation; and wherein at least 70% of the X groups is SO₃M.

In a fourth aspect, the present invention provides a use of an immune checkpoint modulator and a compound of Formula (I) in the manufacture of a medicament for the treatment or prevention of cancer,
wherein the compound of Formula (I) is:

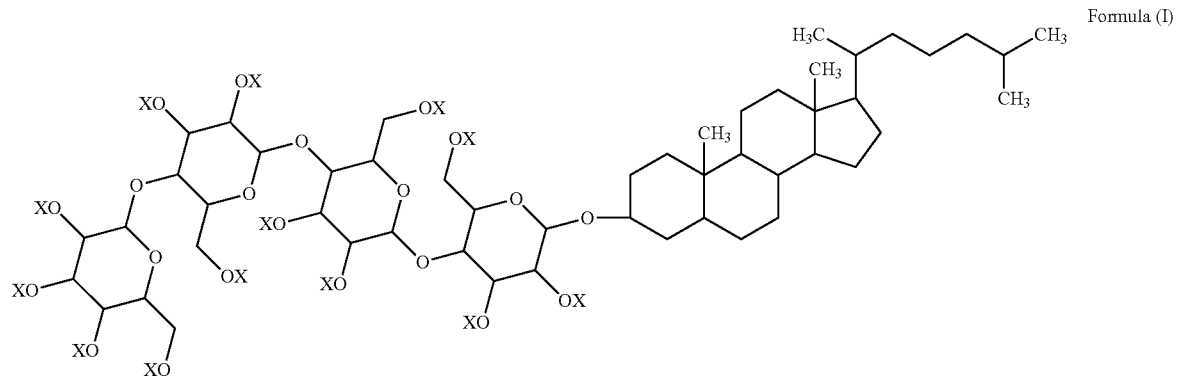

wherein X is SO₃M or H, wherein M is any pharmaceutically acceptable cation; and wherein at least 70% of the X groups is SO₃M.

In a fifth aspect, the present invention provides an immune checkpoint modulator and a compound of Formula (I) for use in the treatment or prevention of cancer; wherein the compound of Formula (I) is:

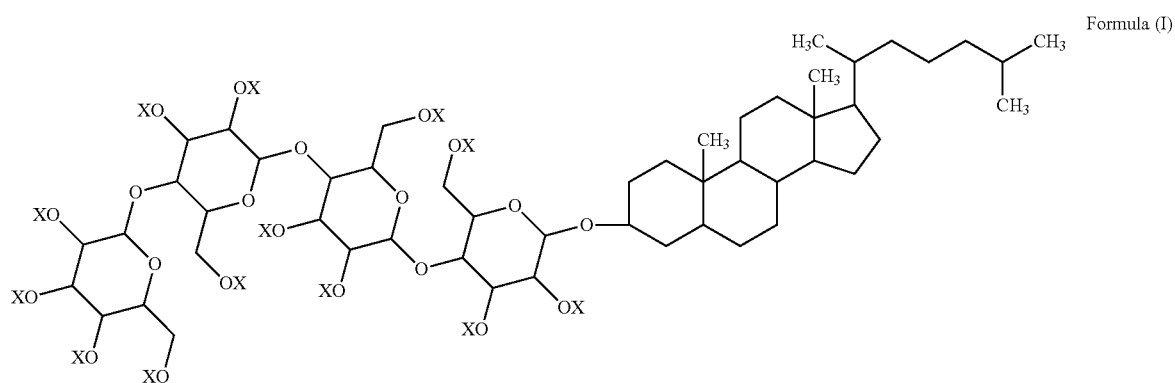

Formula (I)

wherein X is SO₃M or H, wherein M is any pharmaceutically acceptable cation; and wherein at least 70% of the X groups is SO₃M.

In a sixth aspect, the present invention provides a pharmaceutical composition comprising a compound of Formula (I) and an immune checkpoint modulator; wherein the compound of Formula (I) is:

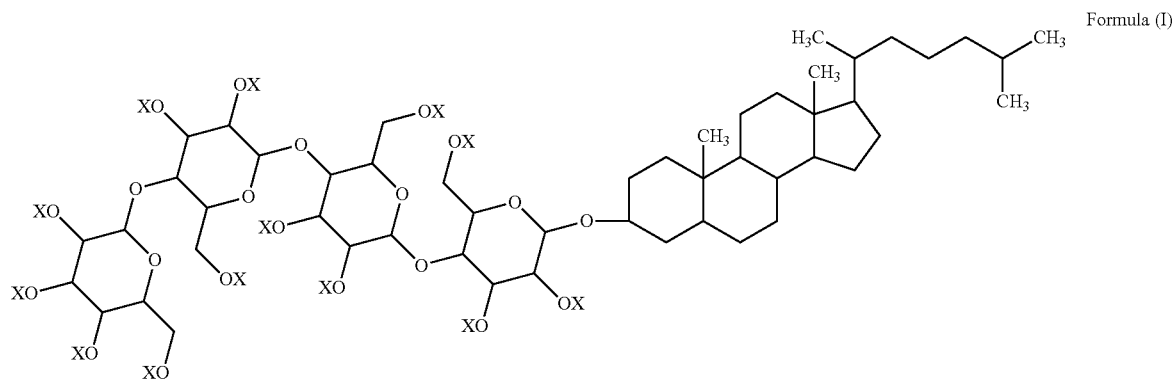

Formula (I)

wherein X is SO₃M or H, wherein M is any pharmaceutically acceptable cation; and wherein at least 70% of the X groups is SO₃M.

Features of the second to sixth aspects of the present invention may be as described for the first aspect of the present invention. The medicament of the second to fourth aspects of the present invention may be a pharmaceutical composition, as described above.

In a seventh aspect, the present invention provides a kit comprising a compound of Formula (I) and an immune checkpoint modulator; wherein the compound of Formula (I) is:

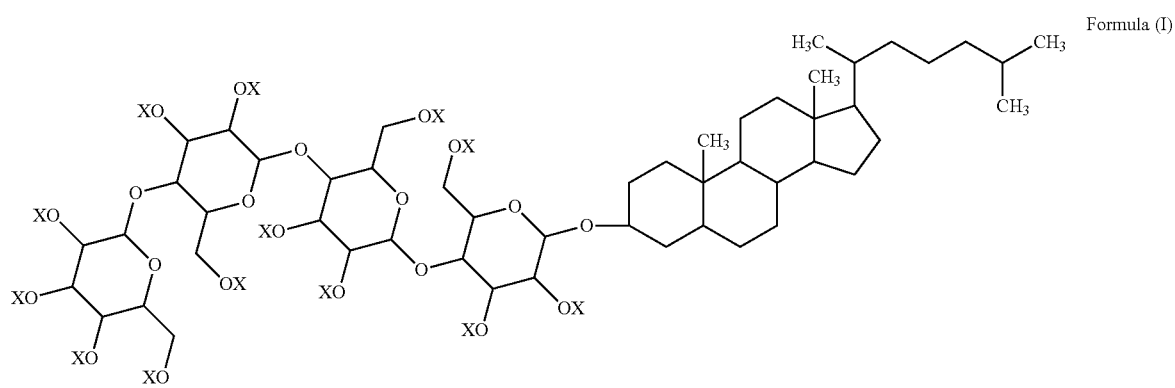

wherein X is SO₃M or H, wherein M is any pharmaceutically acceptable cation; and wherein at least 70% of the X groups is SO₃M.

Features of the seventh aspect of the present invention may be as described for the first to sixth aspects of the present invention. The kit may include a single pharmaceutical composition or at least two pharmaceutical compositions. The kit may include an immune checkpoint modulator and the compound of Formula (I) in the same pharmaceutical composition or in separate pharmaceutical compositions.

In an eighth aspect, the present invention provides a pharmaceutical combination comprising a compound of Formula (I) and an immune checkpoint modulator; wherein the compound of Formula (I) is:

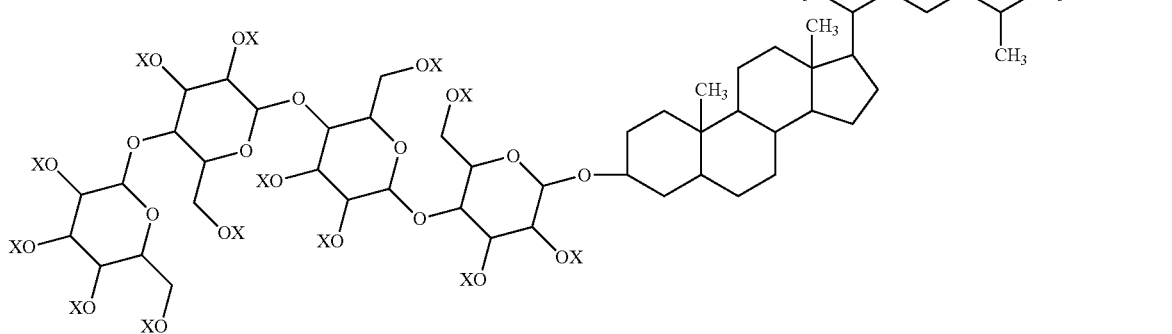

wherein X is SO₃M or H, wherein M is any pharmaceutically acceptable cation; and wherein at least 70% of the X groups is SO₃M.

Features of the eighth aspect may be as described for the first to seventh aspects of the present invention. The pharmaceutical combination may be a pharmaceutical composition, or the pharmaceutical combination may include at least two pharmaceutical compositions. The pharmaceutical combination may include an immune checkpoint modulator and the compound of Formula (I) in the same pharmaceutical composition or in separate pharmaceutical compositions.

In a ninth aspect, the present invention provides a method of enhancing an immune response in a patient, comprising administering to a patient in need thereof an immune checkpoint modulator together with a compound of Formula (I):

FIG. 8 shows therapy-induced changes in 4T1.2 tumour and spleen associated CD4 T cell frequency;

FIG. 9 shows flow cytometric analysis demonstrating the tumour-associated changes in the CD4 T cell compartment within each treatment group (concatenated results shown for each treatment group (4 tumours/group));

FIG. 10 shows therapy-induced changes in 4T1.2 tumour and spleen associated NK cell frequency;

FIGS. 11A and 11B shows the gating strategy for analysing the NK cell responses to therapy in the 4T1.2 mammary tumours;

FIG. 12 shows therapy-induced changes in 4T1.2 tumour myeloid cell frequency;

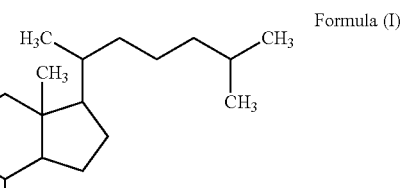
Formula (I)

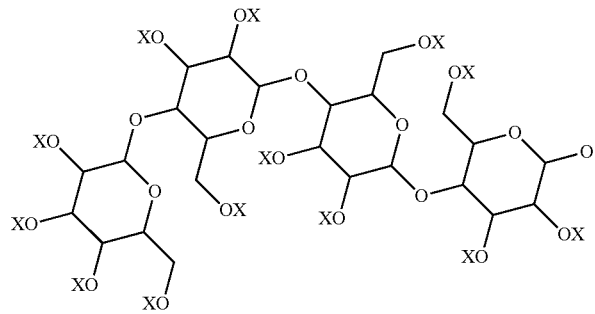

wherein X is SO₃M or H, wherein M is any pharmaceutically acceptable cation; and wherein at least 70% of the X groups is SO₃M.

Features of the ninth aspect of the present invention may be as described for the first to eighth aspects of the present invention.

Any of the features described herein can be combined in any combination with any one or more of the other features described herein within the scope of the invention.

BRIEF DESCRIPTION OF DRAWINGS

Examples of the invention will now be described by way of example with reference to the accompanying Figures, in which:

FIGS. 6A and 6B shows the gating strategy for analysing the CD8 T responses to therapy in the 4T1.2 mammary tumours;

FIG. 13B shows the gating strategy for analysing the myeloid cell responses to therapy (Group 2—PG545+Control antibody) in the 4T1.2 mammary tumours;

FIG. 13C shows the gating strategy for analysing the myeloid cell responses to therapy (Group 3—Vehicle+Anti-PD-1) in the 4T1.2 mammary tumours;

FIG. 13D shows the gating strategy for analysing the myeloid cell responses to therapy (Group 4—PG545+Anti-PD-1) in the 4T1.2 mammary tumours;

Figure 1:
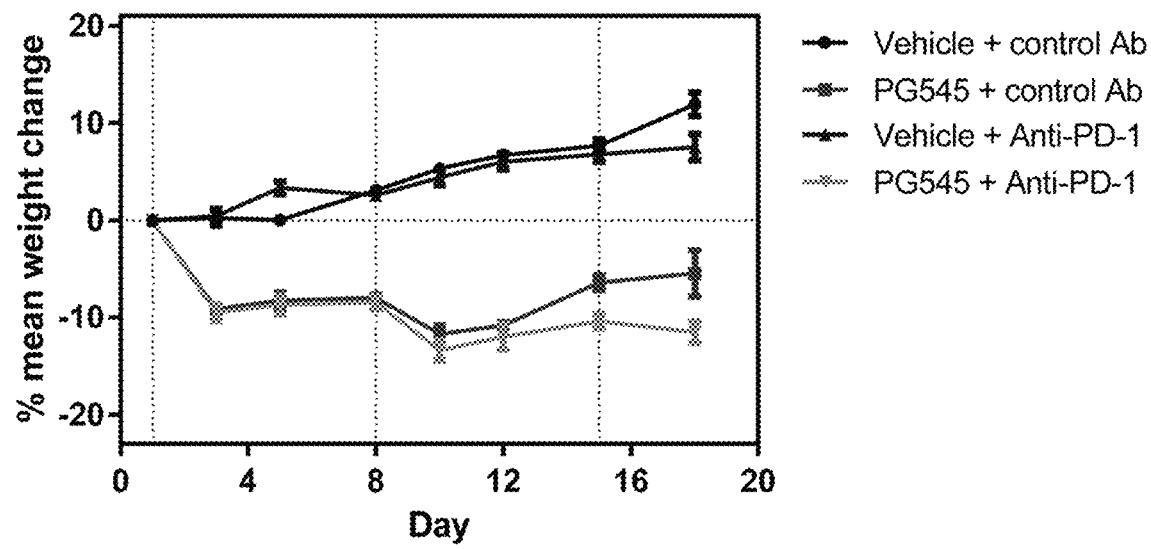
FIG. 1 shows the effect of treatments on 4T1.2 tumour bearing mouse body weight. PG545 was administered intraperitoneally on days 1, 8 and 15 (vertical lines) and antibodies on days 1, 4, 8, 11 and 15.

Preferred features, embodiments and variations of the invention may be discerned from the following Examples which provides sufficient information for those skilled in the art to perform the invention. The following Examples are not to be regarded as limiting the scope of the preceding Summary of the Invention in any way.

EXAMPLES

Examples of the present invention will now be described with reference to FIGS. 1 to 14.
Compounds Used
PG545 (or 3β,5α-Cholestanyl 2,3,4,6-tetra-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-α-D-glucopyranosyl-(1→4)-2,3,6-tri-O-sodium sulfonato-β-D-glucopyranoside), has the structure below. PG545 has been allocated a proposed International Nonproprietary Name (INN) by the World Health Organization of pixatimod (for the acid). This compound is described in WO2009/049370. PG545 may be synthesised as provided in Ferro et al 2012 or in WO2009/049370.

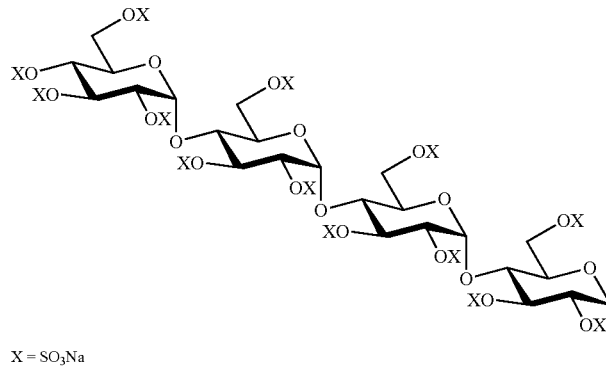
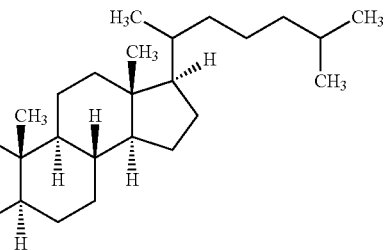

X = SO₃Na

Anti-PD-1 antibody (RMP1-14) was purchased from Bio-X-Cell (NH, USA).

Isotype Control antibody (2A3) was purchased from Bio-X-Cell (NH, USA).

Example 1—Study in the 4T1.2 Tumour Model

Female Balb/c mice (Age 8 weeks; Walter and Eliza Hall Institute of Medical Research (WEHI), Victoria Australia) were inoculated in the intramammary fatpad with 1×10⁵ 4T1.2 cells in phosphate buffered saline. 4T1.2 is a mouse mammary tumour model.

Mice were weighed and tumours measured 2-3 times weekly using electronic callipers. Tumour volume (mm³) was calculated as length (mm)/2×width (mm)². One week following implantation mice with similar sized tumours (mean tumour volume 56 mm³) were randomised into 4 groups of 6 animals (Day 1). Treatment groups were saline+ control antibody, PG545+control antibody, saline+anti-PD-1 and PG545+anti-PD-1.

PG545 was given at 15 mg/kg weekly (0.1 ml/10 g body weight) for 3 weeks and anti-PD-1 or control antibody (200 µg; 100 µL of a 2 mg/mL solution) was given intraperitoneally on days 1, 4, 8, 11 and 15. Mice received a small dish containing a food supplement (Ensure mixed with food dust) daily. A dosage of 15 mg/kg PG545 was selected in view of the body weight issues observed at 20 mg/kg PG545 in these mice (i.e. issues with maximum tolerated dose at 20 mg/kg PG545. The maximum tolerated drug dose (MTD) is defined as that causing 10% body weight loss and from which the animals recovered weight to baseline levels within 7-10 days).

The experiment was ended on day 18 or earlier if an ethical endpoint was met. Blood was collected via cardiac bleed and serum was prepared and frozen at −80° C.

The mean body weight changes following the treatments are shown in FIG. 1. In FIG. 1, the data represent the mean percent weight change from day 1 for each group; bars are standard error of the mean (SEM). At day 15 one mouse in the saline+control antibody group was found dead. At day 18: (i) in the PG545+anti-PD-1 group one mouse was found dead, and the remaining mice showed signs of distress (ruffled fur); and (ii) in the PG545+control antibody group four of the six mice were bloated and showed signs of distress (ruffled fur). It was decided to harvest the experiment on day 18.

The percentage tumour growth inhibition was determined according to the following formula: $100 \times (1-\Delta T/\Delta C)$ where $\Delta C$ and $\Delta T$ were calculated by subtracting the mean tumour volume in each group on day 1 of treatment from the mean tumour volume on the day of analysis. Statistical analysis of the in vivo data was performed using Graph Pad Prism Version 6.0 (Graph Pad La Jolla, Calif.). An ANOVA analysis was performed followed by Dunnett's post hoc test to compare the tumour growth in the treated groups to the vehicle control.

Figure 2:
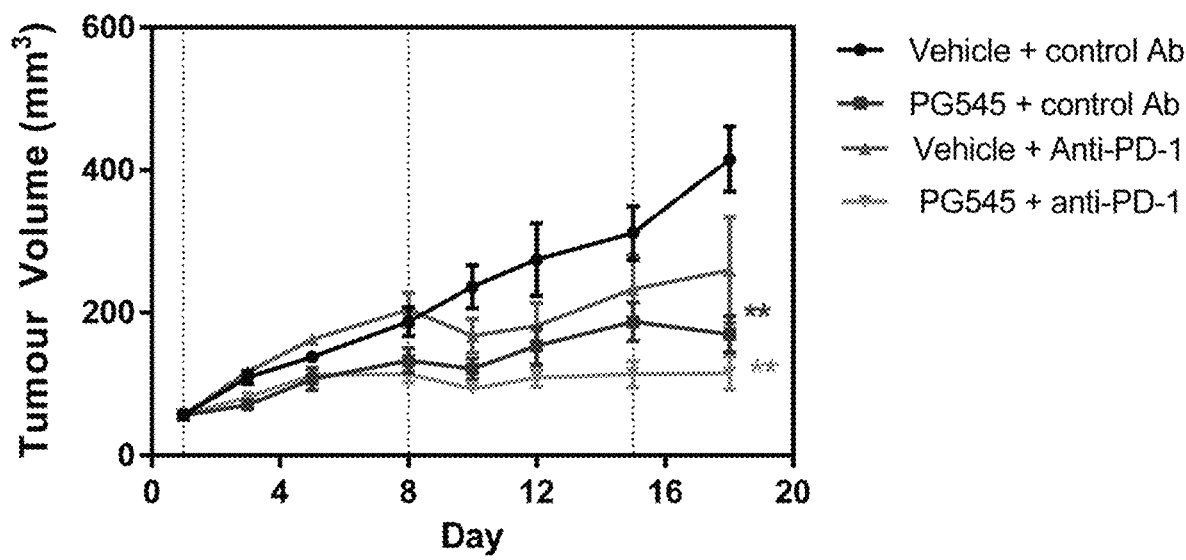
FIG. 2 shows the anti-tumour activity of PD-1 antibody and PG545 alone and in combination against 4T1.2 tumours in vivo.

FIG. 2 summarises the effect of the treatment on 4T1.2 tumour growth. Tumour growth in the PG545+control antibody, saline (or vehicle)+anti-PD-1 and PG545+anti-PD-1 groups was inhibited by 68%, 44% and 84%, respectively on day 18. Tumour growth in the PG545+control antibody and PG545+anti-PD-1 groups was significantly inhibited compared to the saline (or vehicle)+control antibody group (P<0.01 for both). No significant differences were seen between any other groups. In FIG. 2, tumour volumes are expressed as mean tumour volume (±SEM); **=P<0.01 compared to vehicle+control antibody.

Example 2—Study to Evaluate Tumour Infiltrating Leukocytes

Sixteen mice from the cohort implanted in Example 1 above were randomised 1 week after inoculation into 4 groups of 4 mice as for Example 1 (mean tumour volume=77 mm³). PG545 was given intraperitoneally at 15 mg/kg (0.1 ml/10 g body weight) on days 1 and 8 with anti-PD-1 or control antibody (100 µl) given intraperitoneally on days 1, 4 and 8.

On day 11, mice were euthanized and tumours harvested. The tumours were mechanically disaggregated and then digested in collagenase IV and DNase 1 before being filtered through a cell strainer to yield a single cell suspension. Spleens were also removed and used as background staining controls. Where appropriate, the cells were fixed and permeabilised [Ebioscience or BD Pharmingen Fixation/Permeabilisation Kits; also see the procedure provided in the technical data sheet for BD Cytofix/Cytoperm™ available from www.bdbiosciences.com]. The cells were then incubated with the antibody cocktails summarised in Table 2. Flow cytometry analysis was performed on the LSR II analyser (BD Biosciences).

TABLE 2

Immune Staining Cocktails

| Stain 1 | Stain 2 | Stain 3 | Stain 4 |
| --- | --- | --- | --- |
| CD45.2-eFluor450 | CD45.2-APC | CD45.2-PEcy7 | CD45.2-eFluor450 |
| TCRb-APC-cy7 | TCRb-PE | CD49b-APC | Ly6C-PEcy7 |
| CD8b-PEcy7 | CD4-eFluor450 | CD27-PE | CD11b-APCcy7 |
| CD44-FITC | FoxP3-FITC | CD11b-APCcy7 | Ly6G-BV711 |
| CD62L-BV510 | CD8-PEcy7 | CD69-FITC | CD11c-FITC |
| CD69-PE | NO DAPI | CD335-eFluor450 | MHCII-APC |
| Granzyme B | | DAPI | PD-L1-PE |
| NO DAPI | | | DAPI |

Staining Set Summary:

Stain 1 (fixed group due to Granzyme B intracellular stain). Stopping gate for collection was set on CD45.2 for all groups to remove any bias associated with tumour size.

Stain 2. Did not produce a clear data set and was excluded from further analysis.

Stains 3 and 4. Stopping gate for collection was set on DAPI negative cells (viable cell collection date) for all groups to remove any bias associated with tumour size.

In this study statistical analysis was performed using the Mann Whitney U Test.

Figure 3:
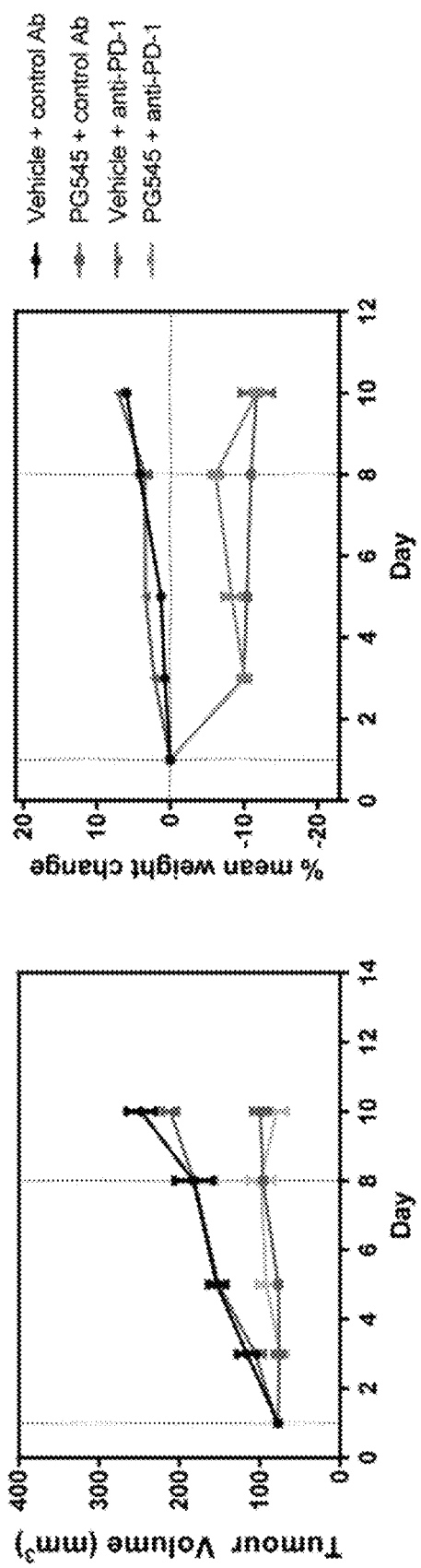
FIG. 3 shows the mean tumour volume and mean weight change of the mice over the course of the study of Example 2.

The mean tumour volume and body weight change of the mice in this study are provided in FIG. 3.

Figure 4:
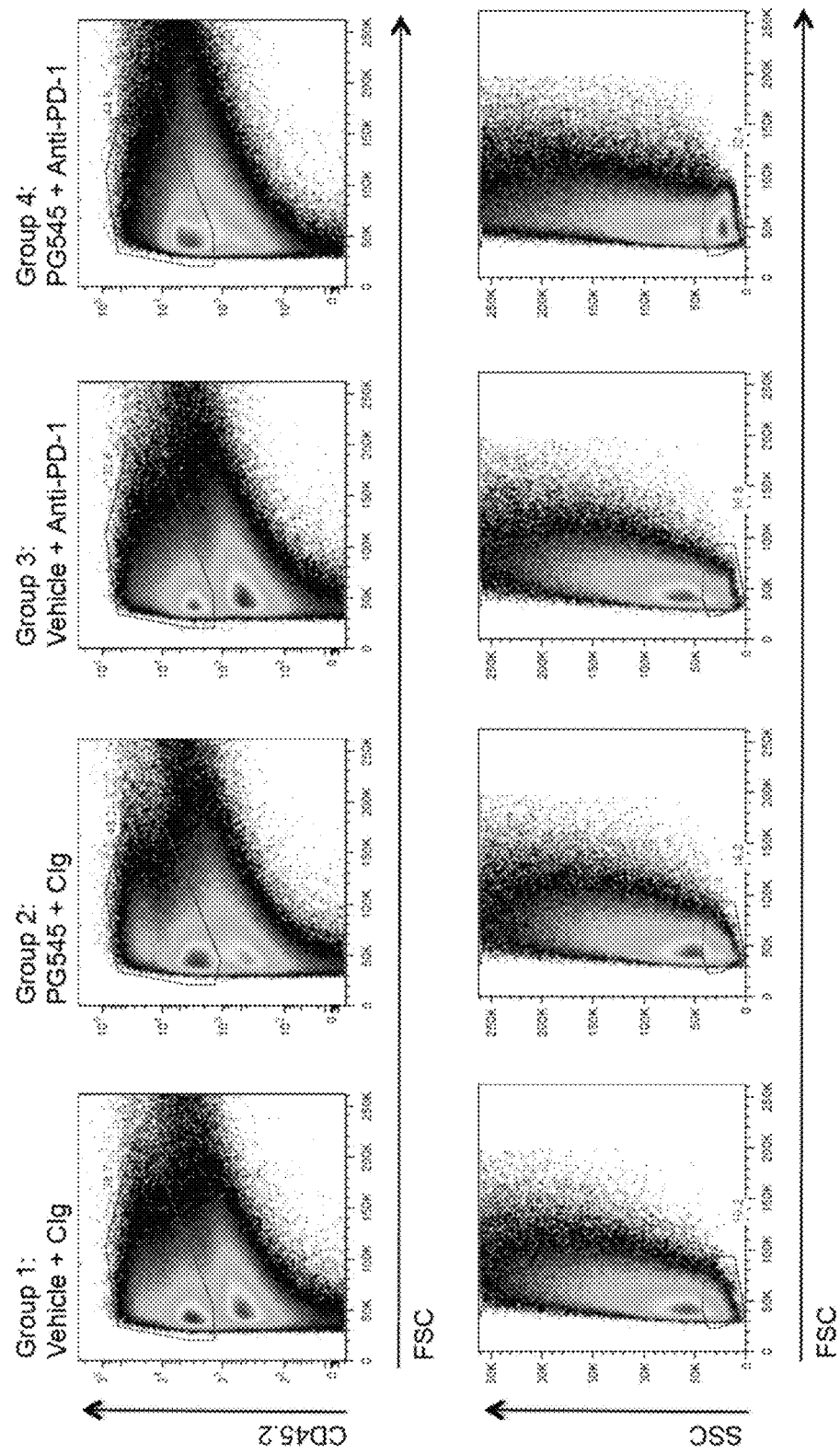
FIG. 4 shows a flow cytometric analysis of the bulk tumour cultures from each treatment group.

A significant increase in lymphocyte frequency was observed within the PG545+anti-PD-1 treated tumours relative to the single agent and control treated tumours (FIG. 4). This increase in 4T1.2 tumour-associated lymphocyte frequency correlated with a reduction in CD45.2 negative cells in the PG545+anti-PD-1 treated tumours; highlighting the impact of the combination therapy on tumour and/or stromal cell viability. In FIG. 4, data shows the concatenated (merged) results from 4 mice in each group. Group 1=Vehicle (saline)+control antibody (CIg); Group 2=PG545+Control antibody; Group 3=Vehicle (saline)+anti-PD-1; Group 4=PG545+anti-PD-1. Row 1 shows the concatenated fluorescence-activated cell sorting (FACs) blots for CD45.2 versus FSC. Row 2 shows the concatenated FACs blots for SSC versus FSC (morphology plot) on the CD45+leukocyte gate.

Figure 5:
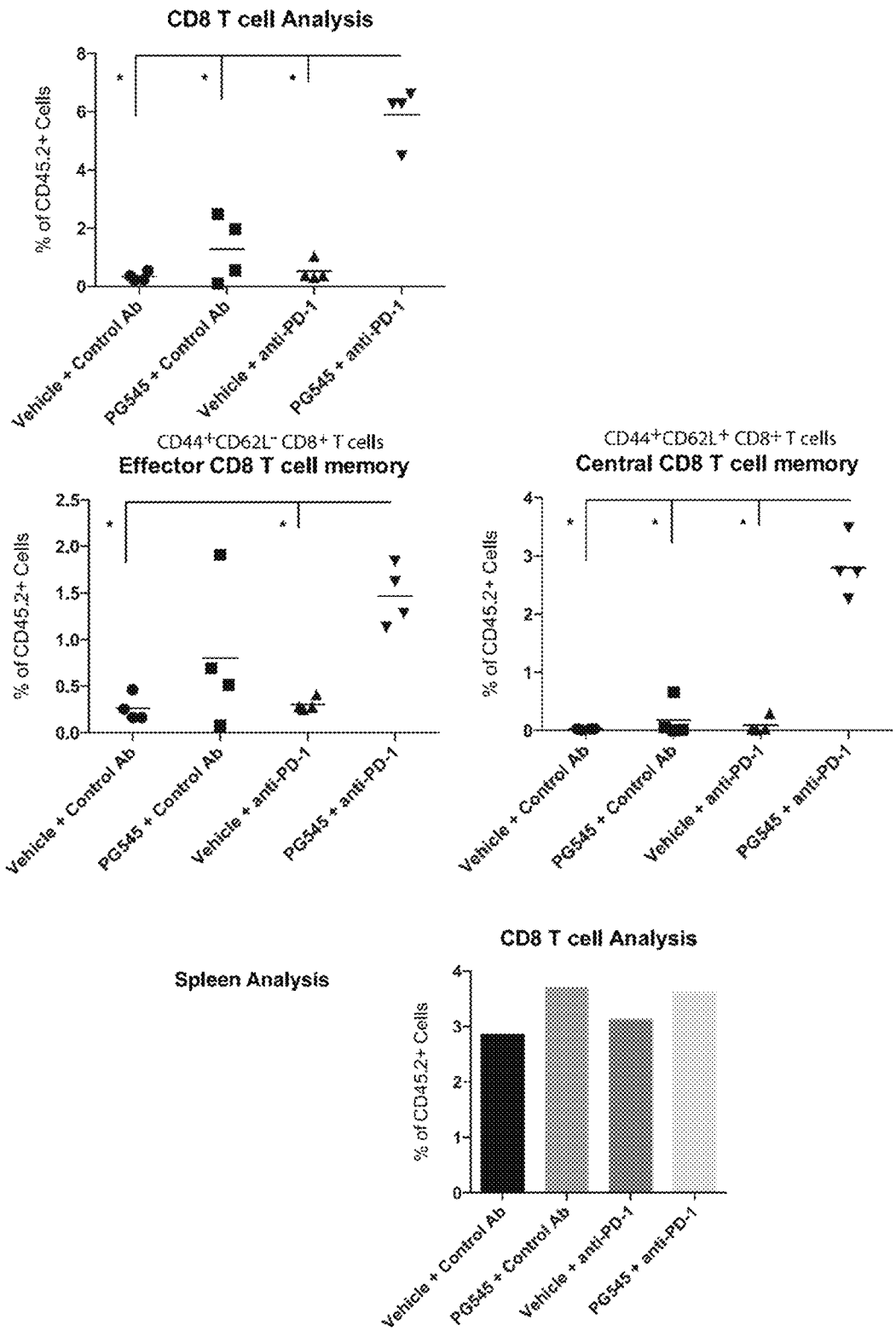
FIG. 5 shows therapy-induced changes in 4T1.2 tumour and spleen associated CD8 T cell frequency.

The increase in tumour-associated lymphocytes in response to PG545+anti-PD-1 treatment correlated with a significant increase in both CD8 (TCRb+CD8+) and CD4 (TCRb+CD8−) T cells (FIG. 5; FACS data collected for Stain 2 was deemed uninterruptible, so the treatment-associated effects on CD4+T effector cells and T regulatory cells was not accurately quantitated). The gating strategy used to analyse Stain 1 is shown in FIG. 6 (in which concatenated results are shown for each treatment group (4 tumours/group)). Notably these therapy-induced changes in T cell frequency were not observed in the spleen (FIG. 5); highlighting the tumour-specific nature of these effects. In FIG. 5, each symbol represents an individual tumour. The horizontal line shown in each treatment group represents the average frequency of tumour-associated CD8 T cells for the group of 4 mice. Spleens from each treatment group were combined for analysis. Each horizontal bar represents the average splenic associated CD8 T cell frequency for each treatment group.

Figure 7:
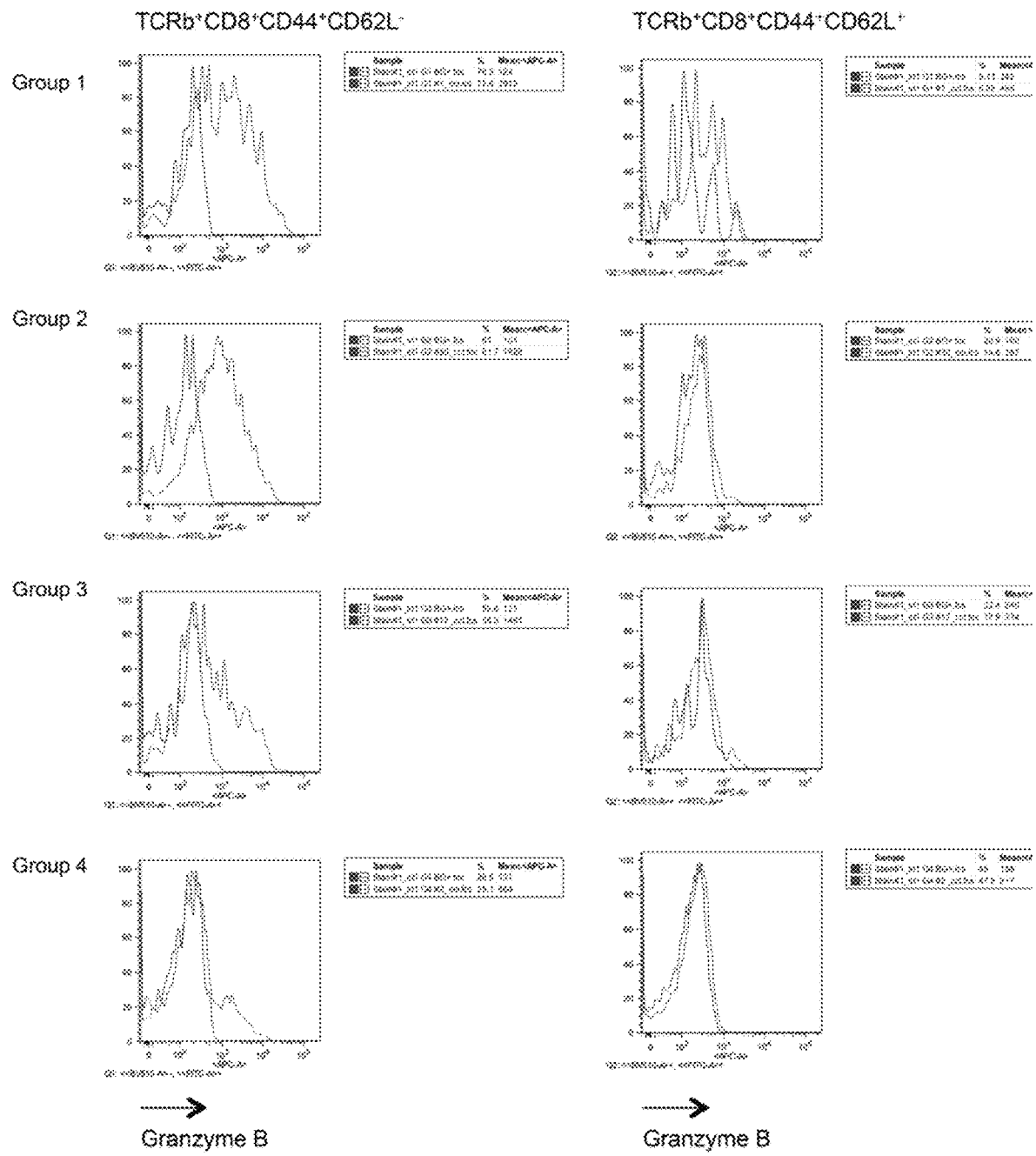
FIG. 7 shows histograms demonstrating the granzyme B status for both the tumour-associated effector and central memory CD8 T cell populations in each treatment group.

Within the tumour-associated CD8+ T cell compartment, a significant increase in the frequency of Central Memory CD8− T cells (CD62L+CD44+ cells) was observed (FIG. 5). Within the PG545+anti-PD-1 treated tumours the frequency of Effector Memory CD8+ T cells was elevated relative to the control and anti-PD-1 treated groups (FIG. 5). However, the frequency of CD69+Granzyme B+Effector CD8+ T cells appeared comparable across the four treatment groups (FIGS. 6 and 7). In FIG. 7, concatenated results are shown for each treatment group (four tumours/group).

Figure 8:
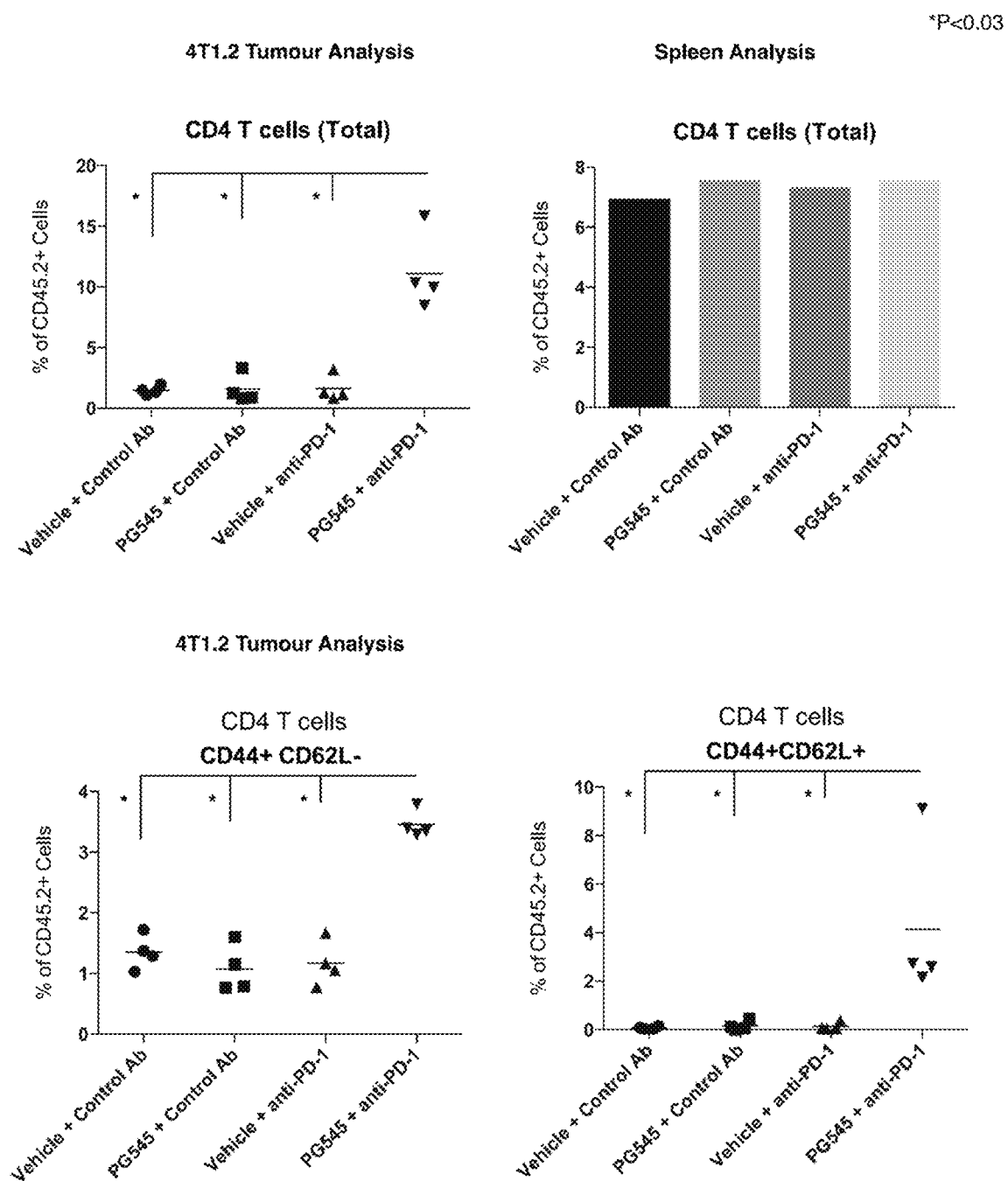
Figure 9:
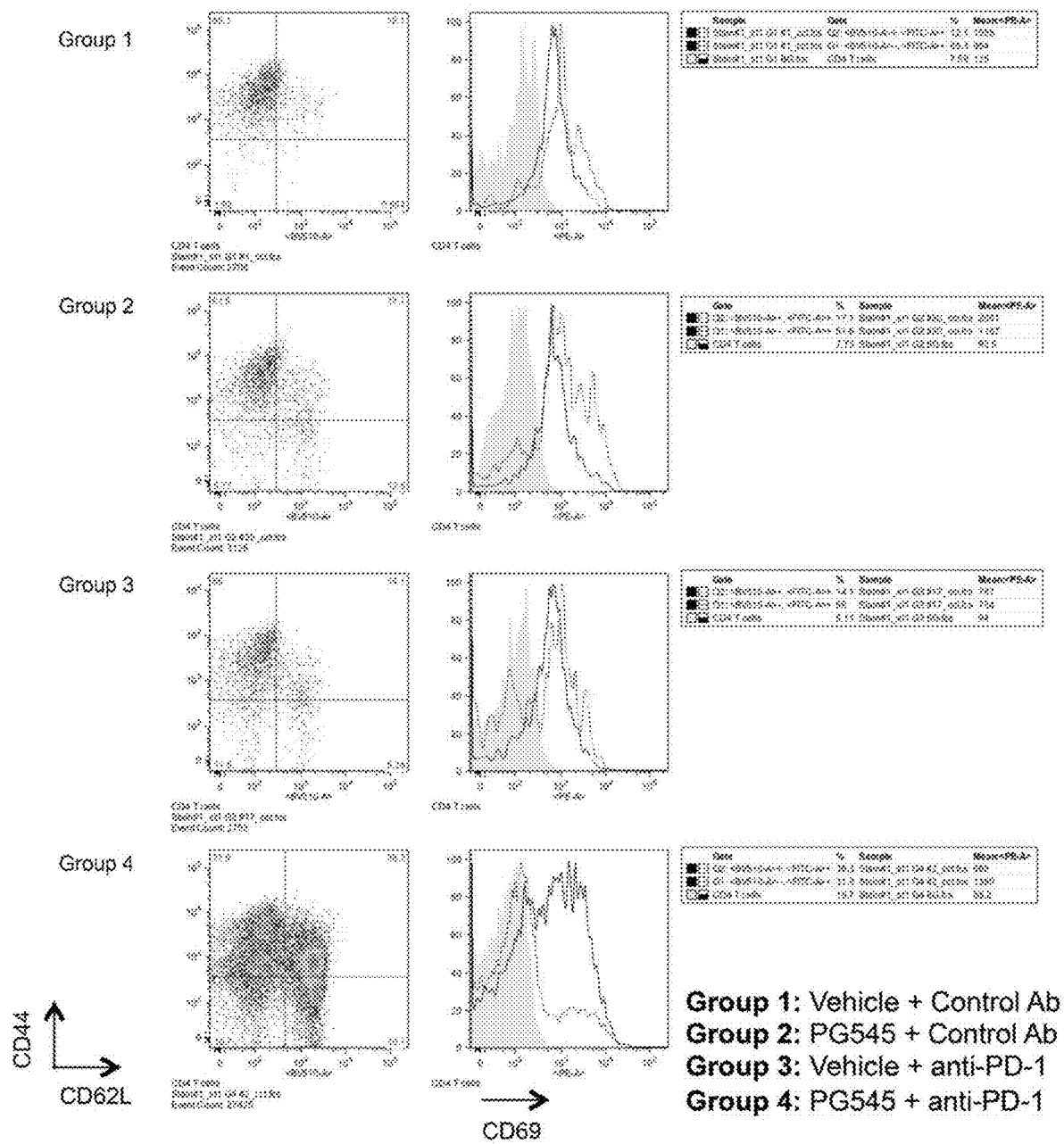

The frequency of tumour-associated $CD4^+CD44^+CD62L^+$ and $CD4^+CD44^+CD62L^-$ T cells was elevated in the PG545+anti-PD-1 group compared to the single agent and control groups (FIG. 8, FIG. 9). These changes in the CD4 T cell compartment of the PG545+anti-PD-1 treated tumours were not evident within the spleens of these mice (FIG. 8), again highlighting the tumour-specific nature of these effects. In FIG. 8, each symbol represents an individual tumour. The horizontal line shown in each treatment group represents the average frequency of tumour-associated CD4 T cells for the group of four mice. Spleens from each treatment group were combined for analysis. Each horizontal bar represents the average splenic associated CD4 T cell frequency for each treatment group.

Figure 10:
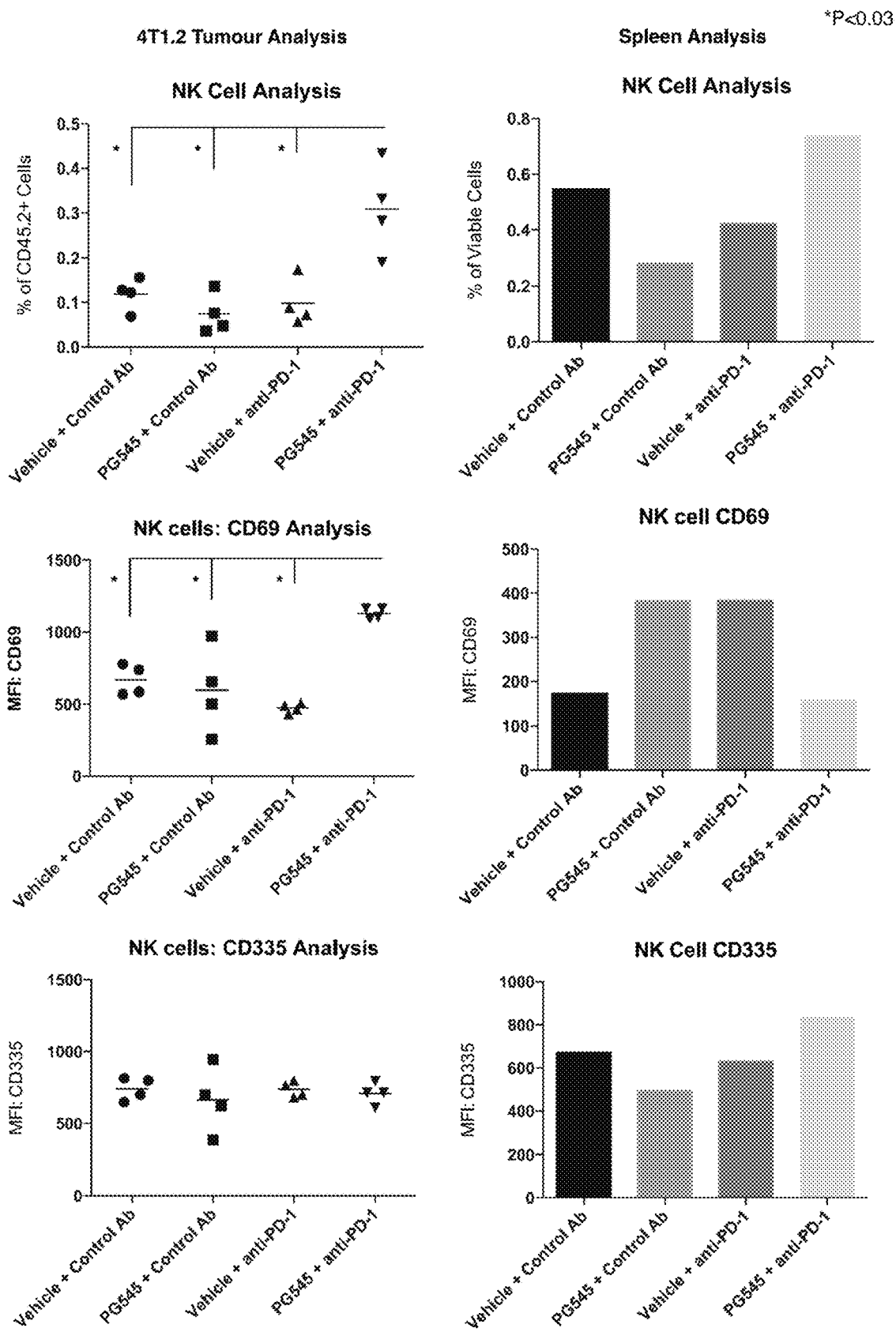
Figure 11A:
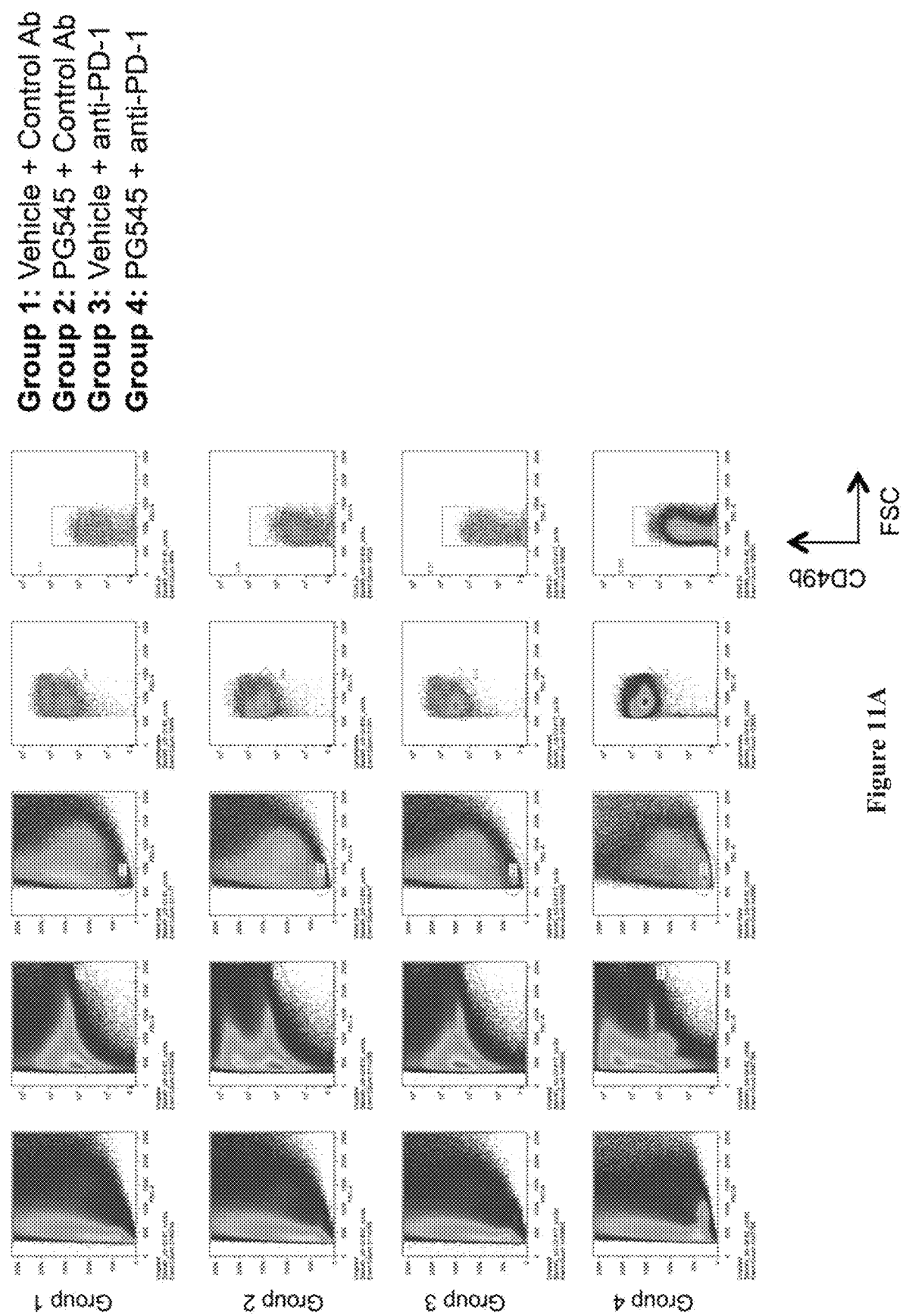
Figure 11B:
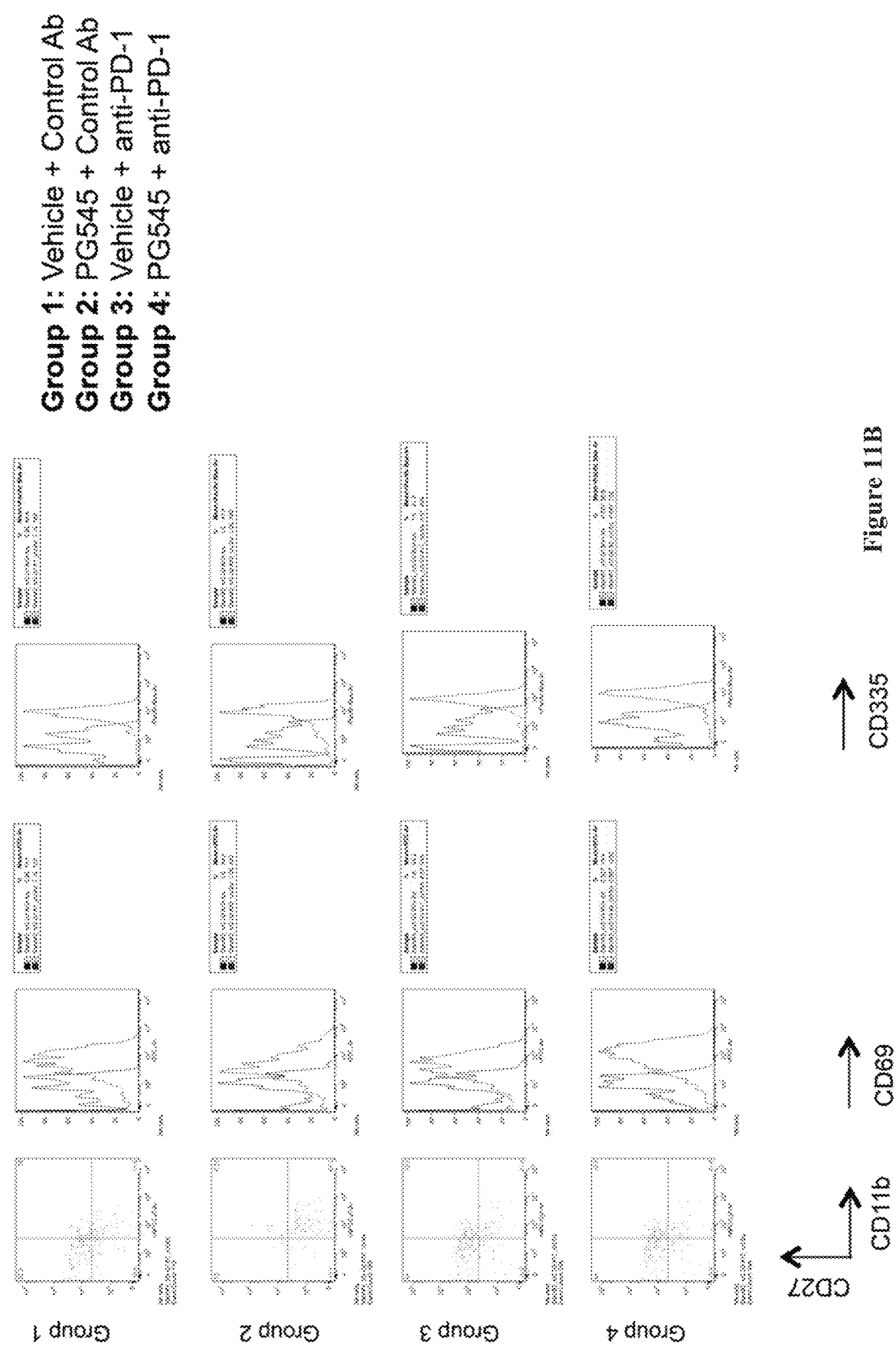

NK cell frequency is low in the 4T1.2 tumours. Co-treatment with PG545+anti-PD-1 significantly increased the frequency of tumour-associated $CD69^+$ NK cells compared to the single agent and control treatments (FIG. 10, FIGS. 11A-11B). Notably this effect of the PG545+anti-PD-1 treatment was not observed within the spleens of these mice. Therapy-associated changes in NK cell expression of CD335 expression were not detected (FIG. 10, FIGS. 11A-11B). In FIG. 10, each symbol represents an individual tumour. The horizontal line shown in each treatment group represents the average frequency of tumour-associated NK cells for the group of four mice. Spleens from each treatment group were combined for analysis. Each horizontal bar represents the average splenic associated NK cell frequency for each treatment group. In FIGS. 11A-11B, concatenated results are shown for each treatment group (four tumours/group).

Figure 12:
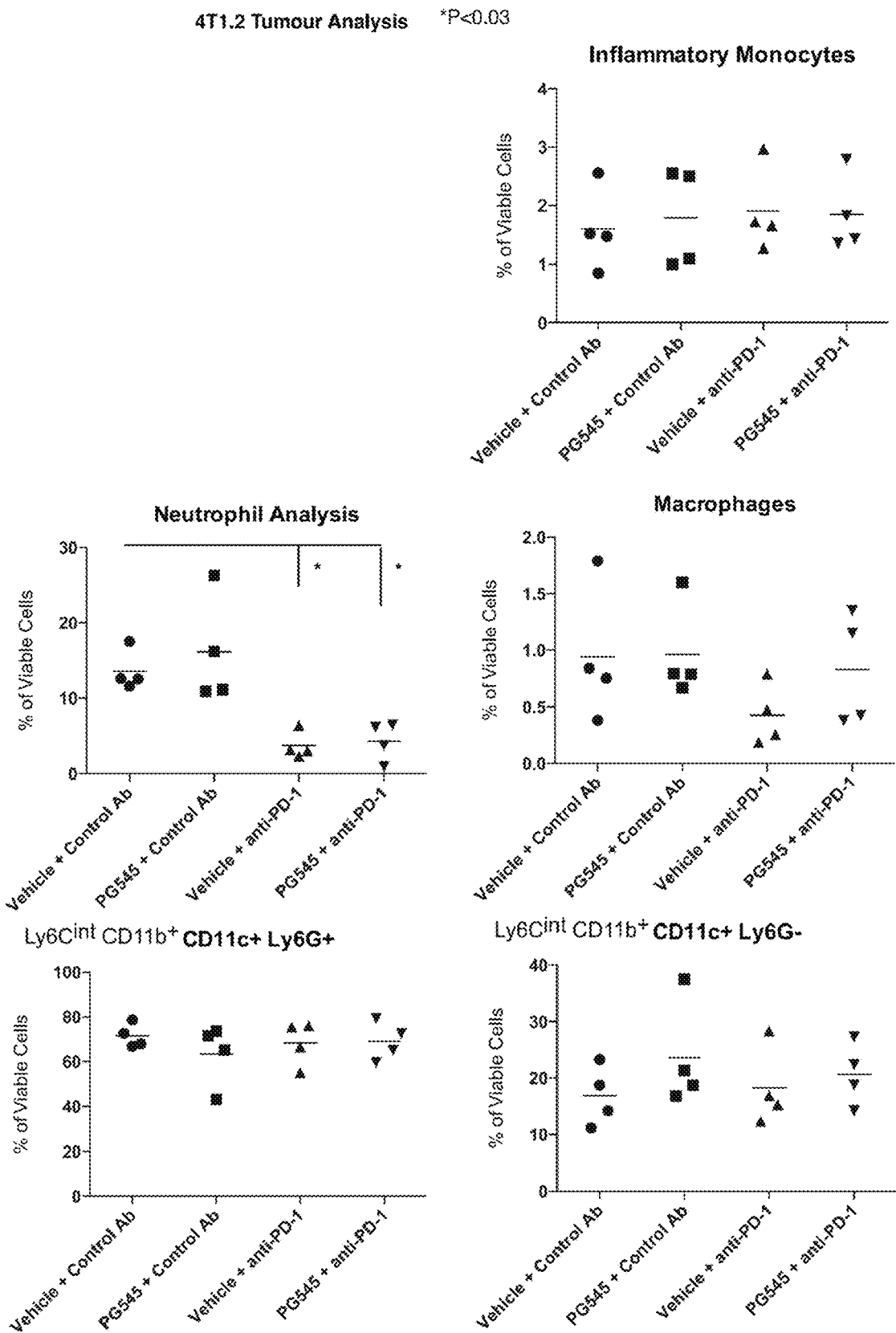
Figure 13A:
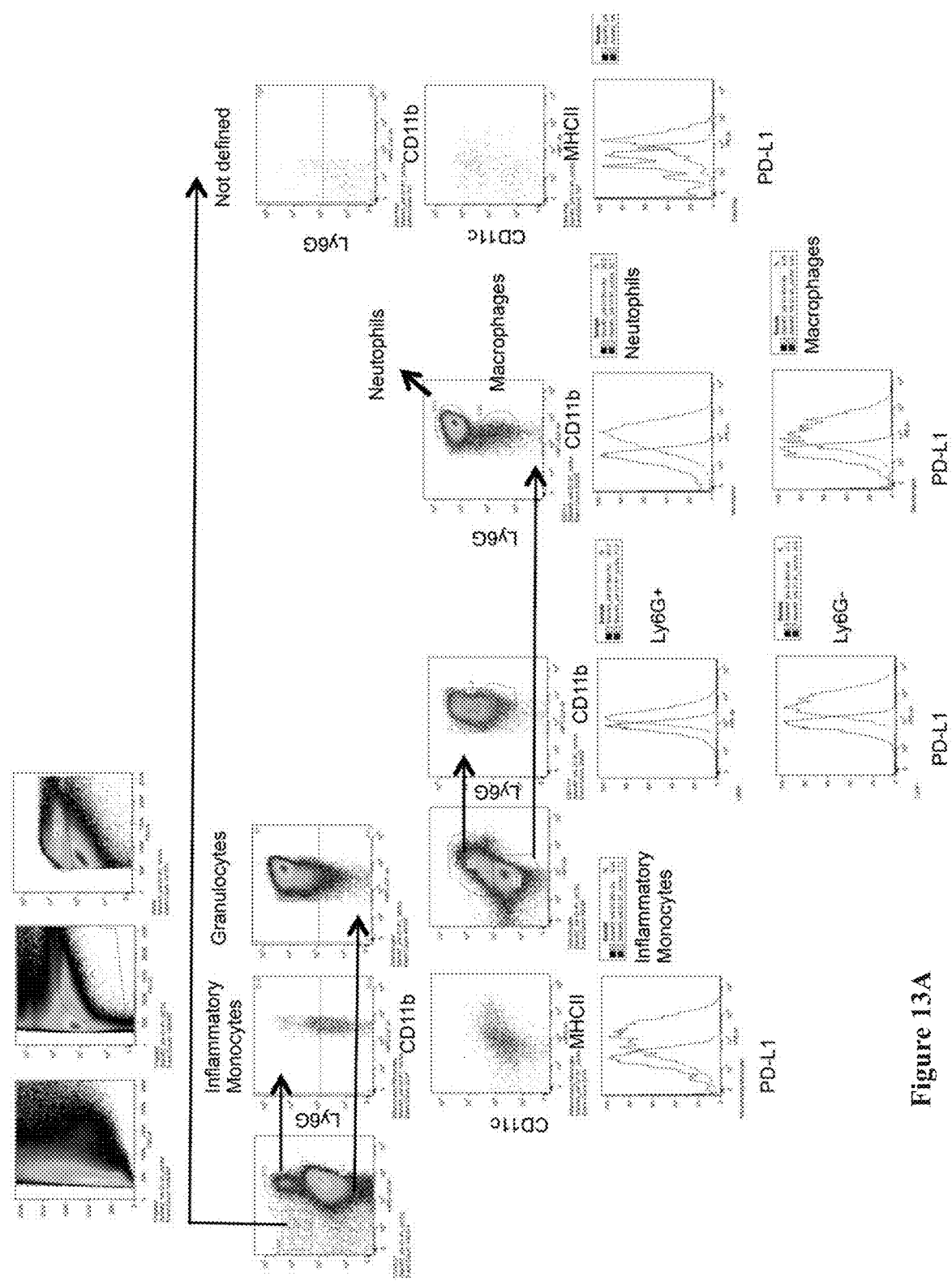
FIG. 13A shows the gating strategy for analysing the myeloid cell responses to therapy (Group 1—Vehicle+Control antibody) in the 4T1.2 mammary tumours.

Drug-associated changes within the 4T1.2 tumour-associated myeloid populations were only observed in the neutrophil cell subset ($Ly6C^{int}CD11b^+CD11^-Ly6G^+$ cells) (FIG. 12; FIGS. 13A-13D (in which concatenated results are shown for each treatment group, four tumours/group)). Anti-PD-1 treatment was the primary mediator of the observed reduction in tumour-associated neutrophils (FIG. 12). In FIG. 12, each symbol represents an individual tumour and the horizontal line shown in each treatment group represents the average frequency of tumour-associated myeloid cells for the group of four mice.

Figure 14:
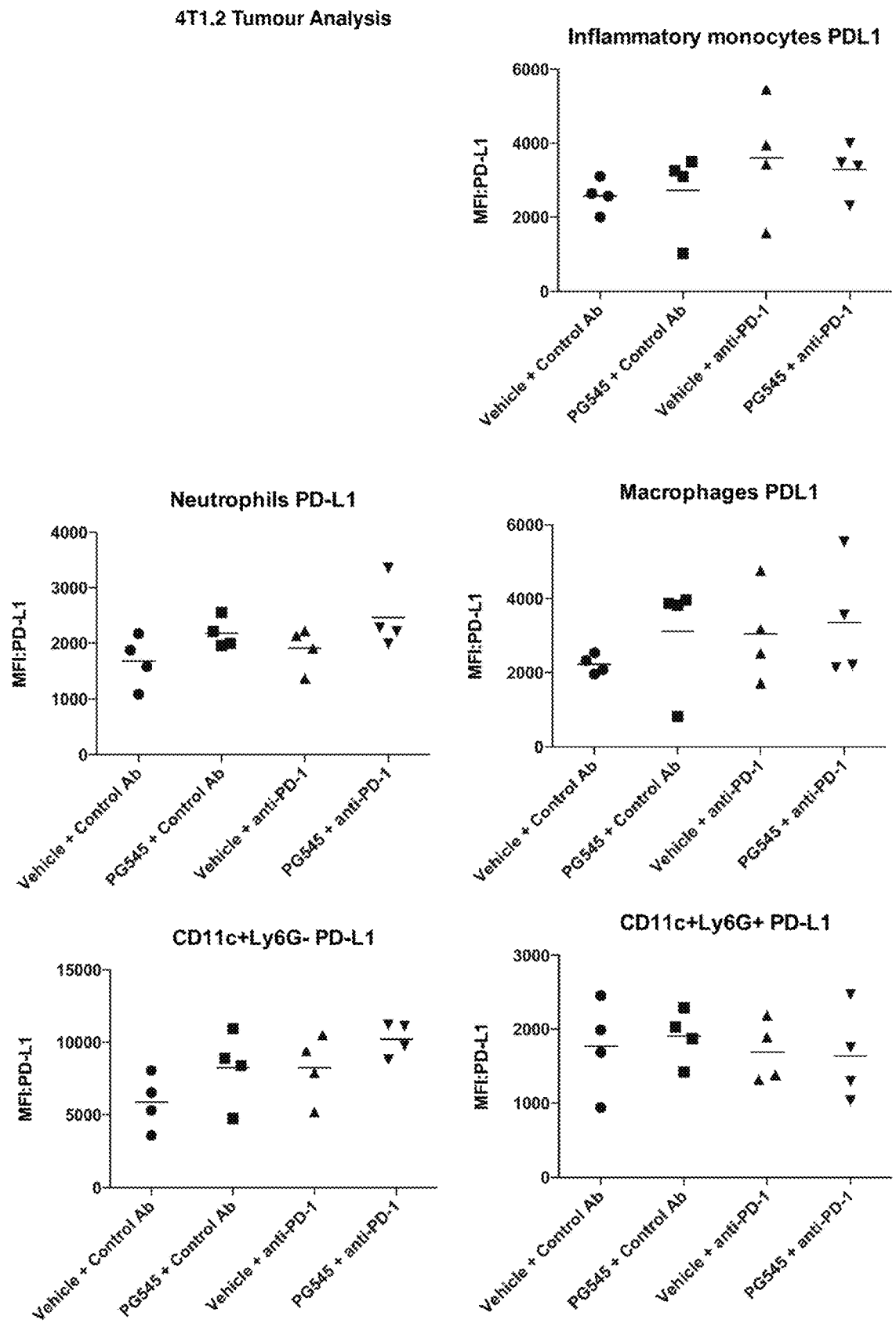
FIG. 14 shows therapy-induced changes in PD-L1 expression on 4T1.2 tumour associated myeloid cells.

Drug-associated changes in PD-L1 expression within the 4T1.2 tumour-associated myeloid compartment were not detected (FIG. 14; FIGS. 13A-13D). In FIG. 14, each symbol represents the mean fluorescence intensity (MFI) for PD-L1 expression within an individual tumour. The horizontal line shown in each treatment group represents the average MFI for PD-L1 expression.

CONCLUSIONS

The % TGI for the PG545 and anti-PD-1 group (84%) was almost two-fold higher compared with the vehicle+anti-PD1 antibody group (44%) and higher than the PG545+control antibody group (68%).

Immune analysis revealed significant synergy of PG545 and anti-PD-1 in the resected 4T1.2 mammary tumours. Significant increases in tumour-associated lymphocytes were observed, with the accumulation of Effector Memory CD8+ T cells, Central Memory CD8+ T cells, and CD4+ T cells in the 4T1.2 tumours.

Synergistic effects of PG545 and anti-PD-1 were also evident on the 4T1.2 tumour-associated NK cells. Significant increases in tumour associated NK cell frequency and CD69 expression within the NK cell compartment were observed in the PG545+anti-PD-1 treated 4T1.2 tumours.

The PG545 and anti-PD1 antibody combination enhanced the TGI almost two-fold compared with anti-PD1 alone. Moreover, synergistic increases in tumour-associated CD8+ T, CD4+T and NK cells were identified in the 4T1.2 tumours treated with both PG545 and anti-PD1 therapy.

Example 3—Human Colorectal Cancer Trial

Five human patients with advanced solid tumours (microsatellite stable colorectal cancer (MSS CRC)) were treated with a combination of PG545 and nivolumab. These patients received a dose of 25 mg PG545 via a 1-hour intravenous infusion administered weekly, and 240 mg nivolumab via an intravenous infusion administered once every two weeks.

The biological activity of the combination was assessed using RECIST v1.1 criteria and by analysing relevant biomarkers of immunomodulation in the peripheral blood. Subjects continued to be treated until they exhibited disease progression (increase of tumour size>20%), were discontinued for reasons of intolerability, or the study was terminated.

Figure 15:
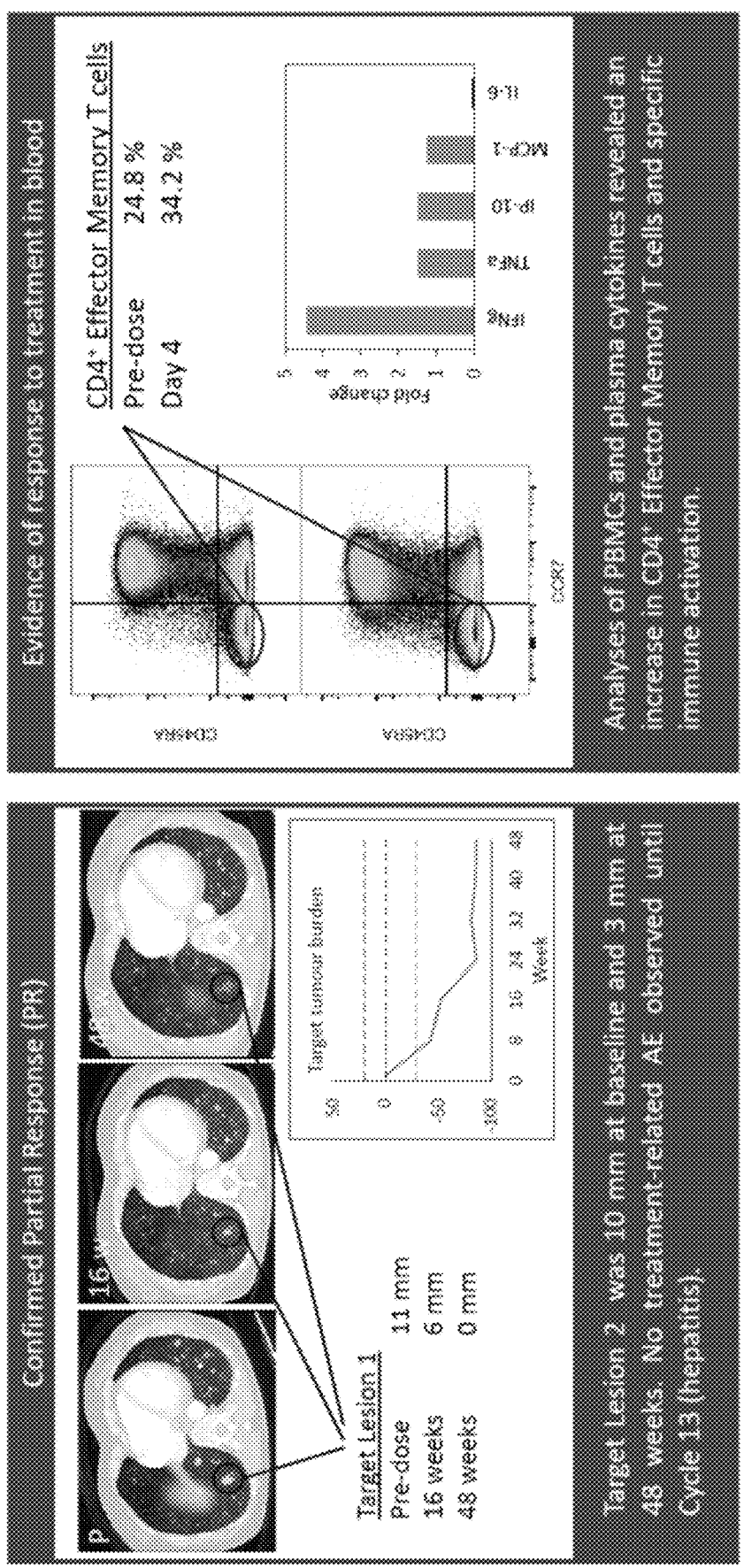
FIG. 15 shows results from administration of PG545 and nivolumab in a first human patient with microsatellite stable colorectal cancer.
Figure 16:
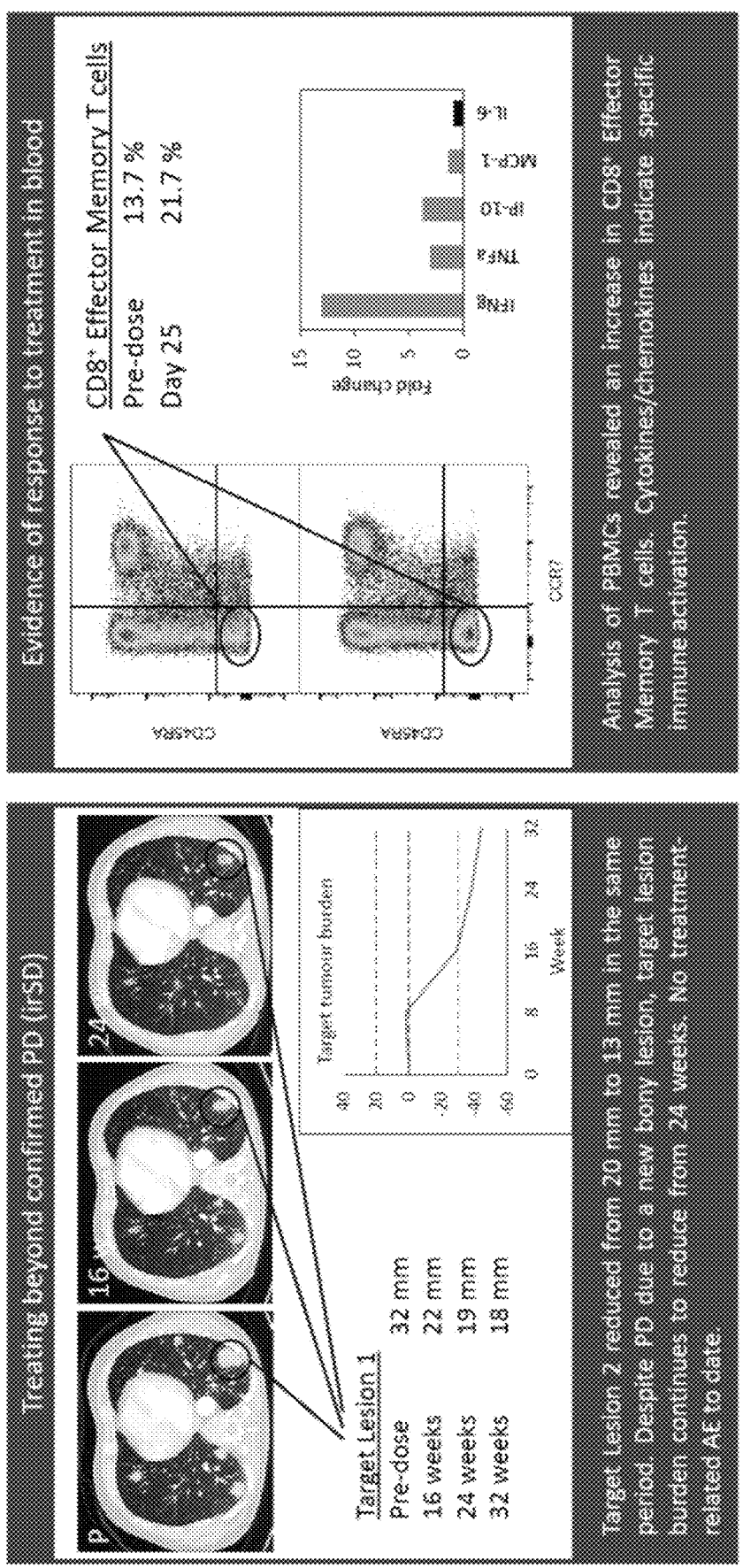
FIG. 16 shows results from administration of PG545 and nivolumab in a second human patient with microsatellite stable colorectal cancer.

The results from two of the patients are provided in FIGS. 15 and 16. These subjects responded to treatment with the combination of PG545 and nivolumab. Moreover, increases in the numbers of effector memory T cells (CD4 or CD8 T cells) were reported in the peripheral blood of these subjects which is consistent with the expansion of T cells reported in tumour-bearing mice (Hammond et al, 2018).

In contrast with these results, a Phase Ia study in patients with advanced solid tumours identified the maximum tolerated dose of PG545 when administered as a once weekly IV infusion, namely 100 mg. However, in that study PG545 monotherapy did not lead to reductions in tumour size (Dredge et al, 2018). Furthermore, despite responses to PD-1 inhibition in microsatellite instability (MSI) high metastatic colorectal cancer (mCRC), no objective response (i.e. tumour shrinkage) has been observed in MSI-low or microsatellite stable (MSS) mCRC subject with nivolumab (Topalian et al. NEJM, 2012) or another PD-1 inhibitor called pembrolizumb (Le et al. Annals of Oncol, 2016). Therefore, the combination of PG545 and the PD-1 inhibitor nivolumab clearly has a synergistic effect on these tumours that could not have been expected based on the activity of either of PG545 or nivolumab alone.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

CITATION LIST

Boyango I, Barash U, Naroditsky I, Li J P, Hammond E, Ilan N, Vlodavsky I. (2014) Heparanase cooperates with Ras to drive breast and skin tumourigenesis. Cancer Res. 74(16): 4504-14.

Brennan T V, Lin L, Brandstadter J D, Rendell V R, Dredge K, Huang X, Yang Y. (2016) Heparan sulfate mimetic PG545-mediated antilymphoma effects require TLR9-dependent NK cell activation. J Clin Invest. 126(1): 207-19.

Chen Y M. (2016) Immune checkpoint inhibitors for nonsmall cell lung cancer treatment. J Chin Med Assoc. doi: 10.1016/j.jcma.2016.08.005. [Epub ahead of print].

Dredge K, Hammond E, Davis K, Li C P, Liu L, Johnstone K, Handley P, Wimmer N, Gonda T J, Gautam A, Ferro V, Bytheway I. (2010) The PG500 series: novel heparan sulfate mimetics as potent angiogenesis and heparanase inhibitors for cancer therapy. Invest New Drugs. 28(3): 276-83. doi: 10.1007/s10637-009-9245-5.

Dredge K, Brennan T V, Hammond E, Lickliter J D, Lin L, Bampton D, Handley P, Lankesheer F, Morrish G, Yang Y, Brown M P, Millward M (2018) A Phase I study of the novel immunomodulatory agent PG545 (pixatimod) in subjects with advanced solid tumours. British Journal of Cancer 118:1035-1041.

Ferro V, Liu L, Johnstone K D, Wimmer N, Karoli K, Handley P, Rowley J, Dredge K, Li C P, Hammond E, Davis K, Sarimaa L, Harenberg J, and Bytheway I (2012) Discovery of PG545: A Highly Potent and Simultaneous Inhibitor of Angiogenesis, Tumour Growth, and Metastasis. J. Med. Chem. 55(8): 3804-3813. doi: 10.1021/jm201708h.

Hammond E, Handley P, Dredge K, Bytheway I. (2013) Mechanisms of heparanase inhibition by the heparan sulfate mimetic PG545 and three structural analogues. FEBS Open Bio. 3: 346-51. doi: 10.1016/j.fob.2013.07.007.

Hammond E, Haynes N M, Cullinane C, Brennan T V, Bampton D, Handley P, Karoli T, Lanksheer F, Lin L, Yang Y, Dredge K (2018) Immunomodulatory activities of pixatimod: emerging nonclinical and clinical data, and its potential utility in combination with PD-1 inhibitors, Journal for ImmunoTherapy of Cancer 6:54.

Le D T, Uram J N, Wang H, Bartlett B, Kemberling H, Eyring A, Azad N S, Laheru D, Donehower R C, Crocenzi T S, Goldberg R M, Fisher G A, Lee J J, Greten T F, Koshiji M, Kang S M P, Anders R A, Eshleman J R, Vogelstein B, Diaz L A (2016) Programmed death-1 blockade in mismatch repair deficient colorectal cancer, Journal of Clinical Oncology 34(15_suppl) 103-103.

Mennitto A, Grassi P, Ratta R, Verzoni E, Prisciandaro M, Procopio G. (2016) Nivolumab in the treatment of advanced renal cell carcinoma: clinical trial evidence and experience. Ther Adv Urol. 8(5): 319-326.

Ostapoff K T, Awasthi N, Cenik B K, Hinz S, Dredge K, Schwarz R E, Brekken R A. (2013) PG545, an angiogenesis and heparanase inhibitor, reduces primary tumour growth and metastasis in experimental pancreatic cancer. Mol Cancer Ther. 12(7): 1190-201.

Spranger S, Sivan A, Corrales L, Gajewski T F (2016) Tumour and Host Factors Controlling Antitumor Immunity and Efficacy of Cancer Immunotherapy. Adv Immunol. 130: 75-93.

Topalian S L, Hodi F S, Brahmer J R, Gettinger S N, Smith D C, McDermott D F, Powderly J D, Carvajal R D, Sosman J A, Atkins M B, Leming P D, Spigel D R, Antonia S J, Horn L, Drake C G, Pardoll D M, Chen L, Sharfman W H, Anders R A, Taube J M, McMiller T L, Xu H, Korman A J, Jure-Kunkel M, Agrawal S, Ph.D., McDonald D, Kollia G D, Gupta A, Wigginton J M, Sznol M, (2012) Safety, Activity, and Immune Correlates of Anti-PD-1 Antibody in Cancer. The New England Journal of Medicine 366(26) 2443-2454.

U.S. Food and Drug Administration (May 17, 2016). "Nivolumab (Opdivo) for Hodgkin Lymphoma". U.S. Food and Drug Administration. U.S. Food and Drug Administration.

Woo S R, Corrales L, Gajewski T F (2015) The STING pathway and the T cell-inflamed tumour microenvironment. Trends Immunol. 36(4): 250-256.

The invention claimed is:

1. A method of treating or preventing cancer, comprising administering to a patient in need thereof an immune checkpoint inhibitor together with a compound of Formula (I):

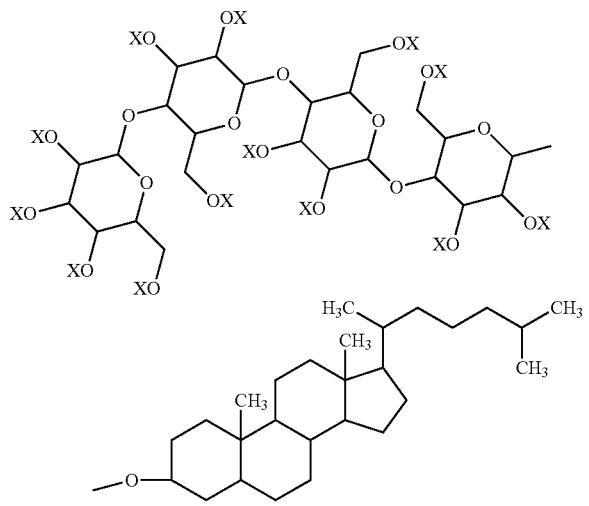

Formula (I)

wherein X is SO$_3$M or H, wherein M is any pharmaceutically acceptable cation;
wherein at least 70% of the X groups is SO$_3$M; and
wherein the immune checkpoint inhibitor is a PD-1 inhibitor or a PD-L1 inhibitor.

2. The method of claim 1, wherein at least 90% of the X groups is SO$_3$M.

3. The method of claim 1, wherein the compound of Formula (I) is a compound of Formula (VI):

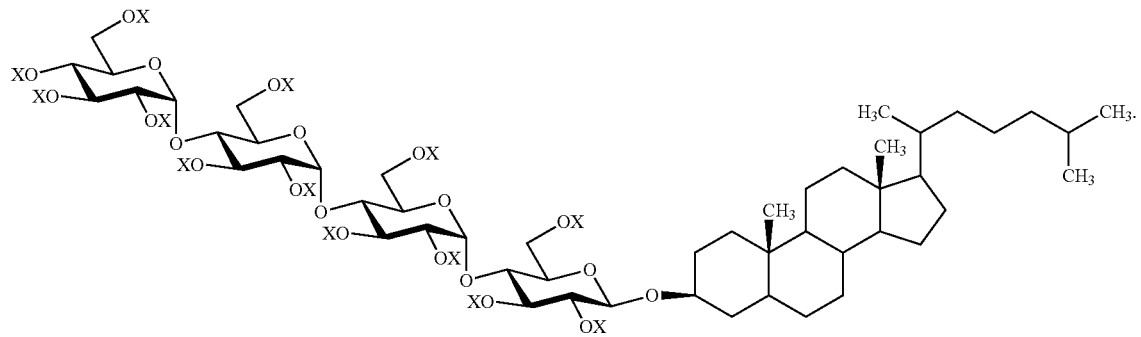

Formula (VI)

4. The method of claim 1, wherein the immune checkpoint inhibitor targets one or more of a T cell, a Natural Killer (NK) cell, a Natural Killer T cell (NKT), a Gamma Delta T cell, an invariant T cell, or an invariant Natural Killer T cell (NKT).

5. The method of claim 1, wherein the immune checkpoint inhibitor is a T cell immune checkpoint inhibitor.

6. A method of treating or preventing cancer, comprising administering to a patient in need thereof Nivolumab together with a compound of Formula (I):

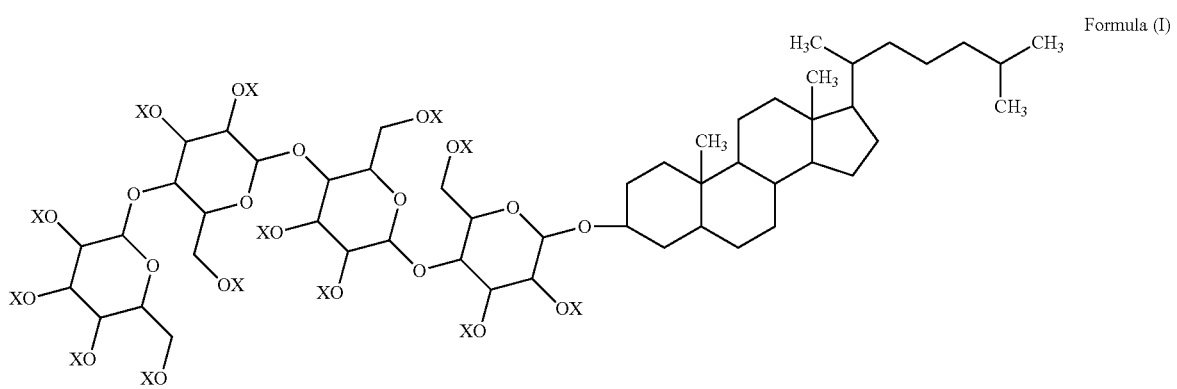

Formula (I)

wherein X is $SO_3M$ or H, wherein M is any pharmaceutically acceptable cation; and wherein at least 70% of the X groups is $SO_3M$.

7. The method of claim 1, wherein the cancer is a solid tumour.

8. The method of claim 3, wherein the method is a method of treating cancer.

9. A pharmaceutical composition or combination comprising a compound of Formula (I) and an immune checkpoint inhibitor, wherein the compound of Formula (I) is:

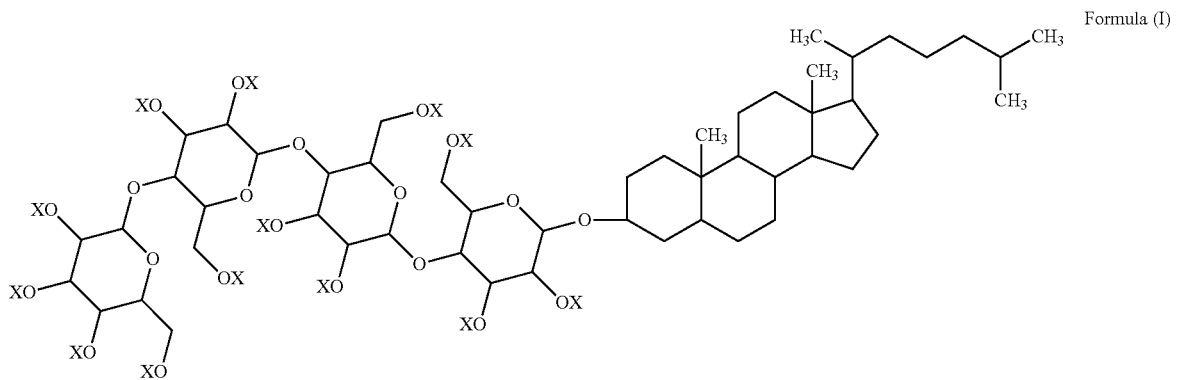

Formula (I)

wherein X is SO₃M or H, wherein M is any pharmaceutically acceptable cation;
wherein at least 70% of the X groups is SO₃M; and
wherein the immune checkpoint inhibitor is a PD-1 inhibitor or a PD-L1 inhibitor.

10. A pharmaceutical composition or combination, comprising a compound of Formula (I) and Nivolumab, wherein the compound of Formula (I) is:

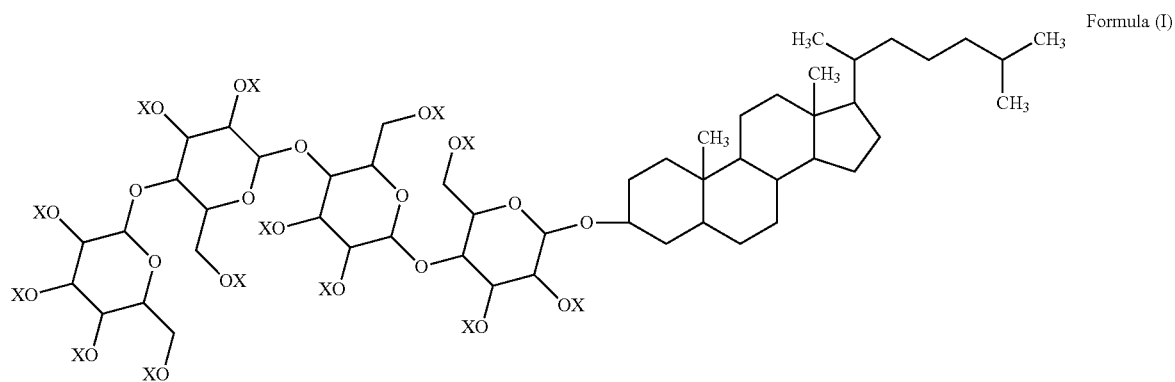

wherein X is SO₃M or H, wherein M is any pharmaceutically acceptable cation; and
wherein at least 70% of the X groups is SO₃M.

11. A kit comprising a compound of Formula (I) and an immune checkpoint inhibitor, wherein the compound of Formula (I) is:

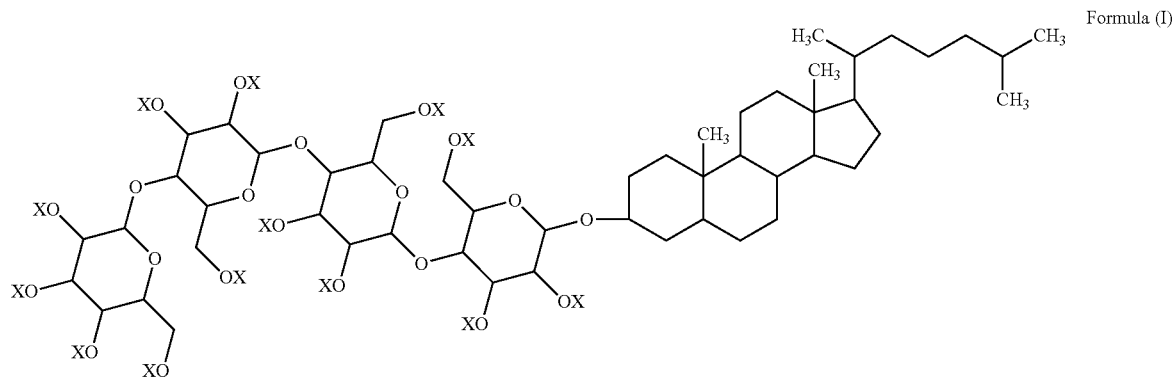

wherein X is SO₃M or H, wherein M is any pharmaceutically acceptable cation;
wherein at least 70% of the X groups is SO₃M; and
wherein the immune checkpoint inhibitor is a PD-1 inhibitor or a PD-L1 inhibitor.

12. The pharmaceutical composition or combination of claim 9, wherein at least 90% of the X groups is SO₃M.

13. The pharmaceutical composition or combination of claim 9, wherein the compound of Formula (I) is a compound of Formula (VI):

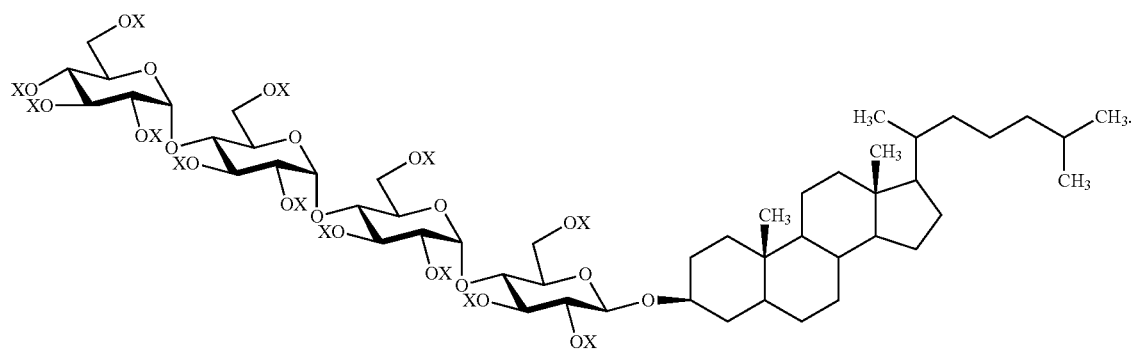

Formula (VI)

14. The kit of claim 11, wherein at least 90% of the X groups is SO₃M.

15. The kit of claim 11, wherein the compound of Formula (I) is a compound of Formula (VI):

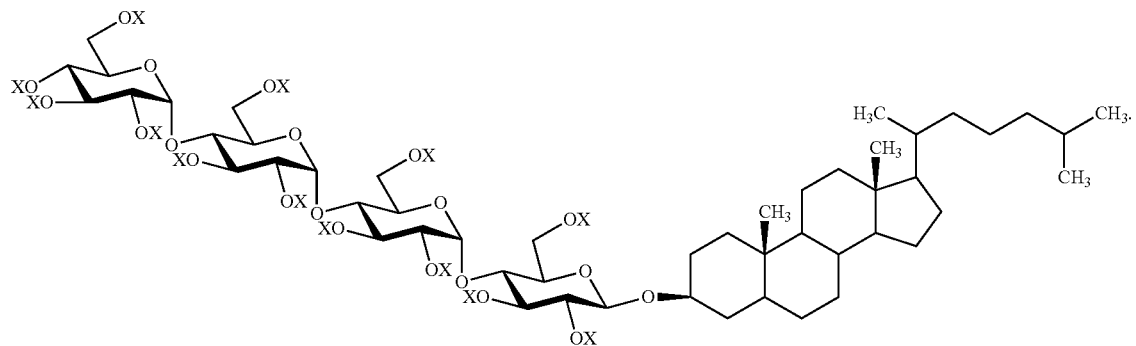

Formula (VI)

16. A kit, comprising a compound of Formula (I) and Nivolumab, wherein the compound of Formula (I) is:

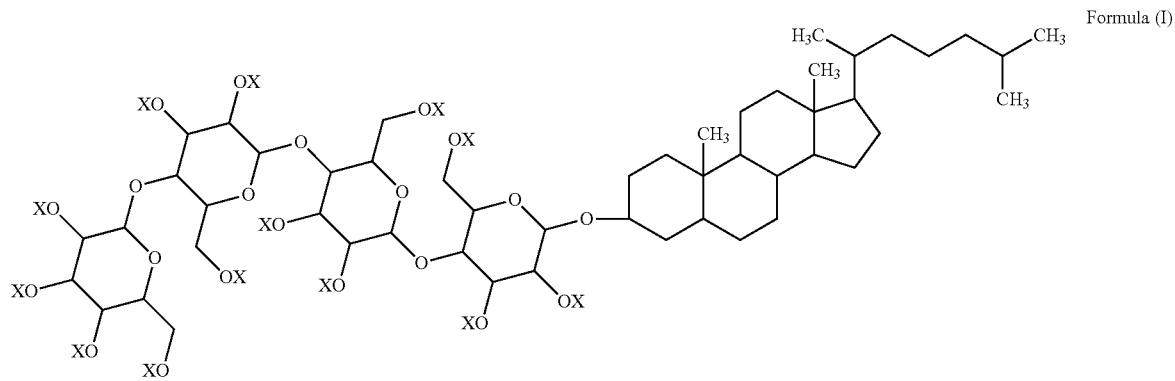

wherein X is SO$_3$M or H, wherein M is any pharmaceutically acceptable cation; and wherein at least 70% of the X groups is SO$_3$M.

17. The method of claim 1, wherein the immune checkpoint inhibitor is a PD-1 inhibitor.

18. The pharmaceutical composition or combination of claim 9, wherein the immune checkpoint inhibitor is a PD-1 inhibitor.

19. The kit of claim 11, wherein the immune checkpoint inhibitor is a PD-1 inhibitor.

* * * * *